(12) United States Patent
Swift et al.

(10) Patent No.: US 6,946,247 B1
(45) Date of Patent: Sep. 20, 2005

(54) RNASE PROBE PROTECTION ASSAYS IN SCREENING FOR MODULATORS OF IMMUNOGLOBULIN GERMLINE TRANSCRIPTION

(75) Inventors: Susan E. Swift, Menlo Park, CA (US); Jakob M. Bogenberger, San Mateo, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 344 days.

(21) Appl. No.: 09/847,960

(22) Filed: May 2, 2001

Related U.S. Application Data
(60) Provisional application No. 60/201,333, filed on May 2, 2000.

(51) Int. Cl.$^7$ .......................... C12Q 1/68; C12N 15/13
(52) U.S. Cl. ........................................ 435/6; 435/440
(58) Field of Search ...................... 435/6, 440

(56) References Cited

PUBLICATIONS

Chan et al., Analytical Biochem. vol. 242 (1996) pp. 214–220.*

Overexpression of BSAP/Pax–5 inhibits switching to IgA and enhances switching to IgE in the 1.29 mu B cell line, Qiu G, Stavnezer J., J. Immunol., Sep. 15, 1998;161(6):2906–18.*

Berton MT, Vitetta Es. IL–4–induced expression of germline gamma 1 transcripts in B cells following cognate interactions with T helper cells. Int Immunol. Mar. 1992;4(3):387–96.

Berton MT, et al. Synthesis of germ–line gamma 1 immunoglobulin heavy–chain transcripts in resting B cells: induction by interleukin 4 and inhibition by interferon gamma. Proc Natl Acad Sci U.S.A. Apr. 1989;86(8):2829–33.

Jardieu P. Anti–IgE therapy. Curr Opin Immunol. Dec. 1995;7(6):779–82.

Shields RL, et al. Inhibition of allergic reactions with antibodies to IgE. Int Arch Allergy Immunol. May–Jun 1995;107(1–3):308–12.

Turaga PS, Berton MT, Teale JM. Frequency of B cells expressing germ–line gamma 1 transcripts upon IL–4 induction J. Immunol. Aug. 1, 1993;151(3):1383–90.

Warren WD, Berton MT. Induction of germ–line gamma 1 and epsilon Ig gene expression in murine B cells. IL–4 and the CD40 ligand–CD40 interaction provide distinct but synergistic signals. J Immunol. Dec. 15, 1995;155(12):5637–46.

* cited by examiner

*Primary Examiner*—Bennett Celsa
(74) *Attorney, Agent, or Firm*—Lahive & Cockfield, LLP; DeAnn F. Smith; Megan E. Williams

(57) ABSTRACT

The present invention relates to the field of immunology, and more particularly to the regulation of antibody idiotypes. Provided are compositions and methods for determining and quantitating immunoglobulin germline transcript expression. As disclosed herein, these methods can be used to screen a plurality of candidate agents to identify a candidate agent capable of modulating an immunoglobulin germline transcript. Further, these methods can be used to identify a candidate agent having different modulatory effects on distinct immunoglobulin germline transcripts.

21 Claims, 9 Drawing Sheets

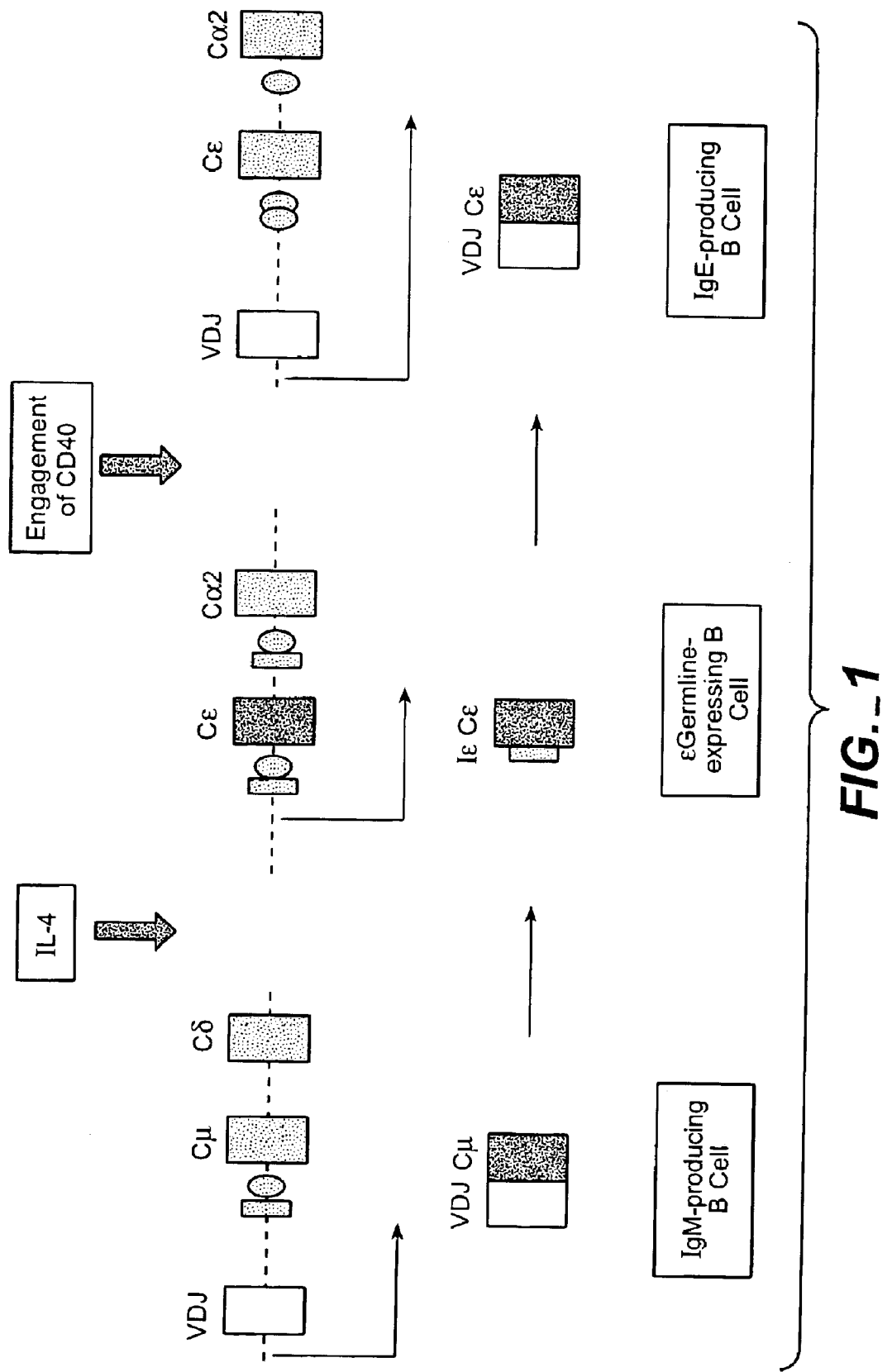
FIG._1

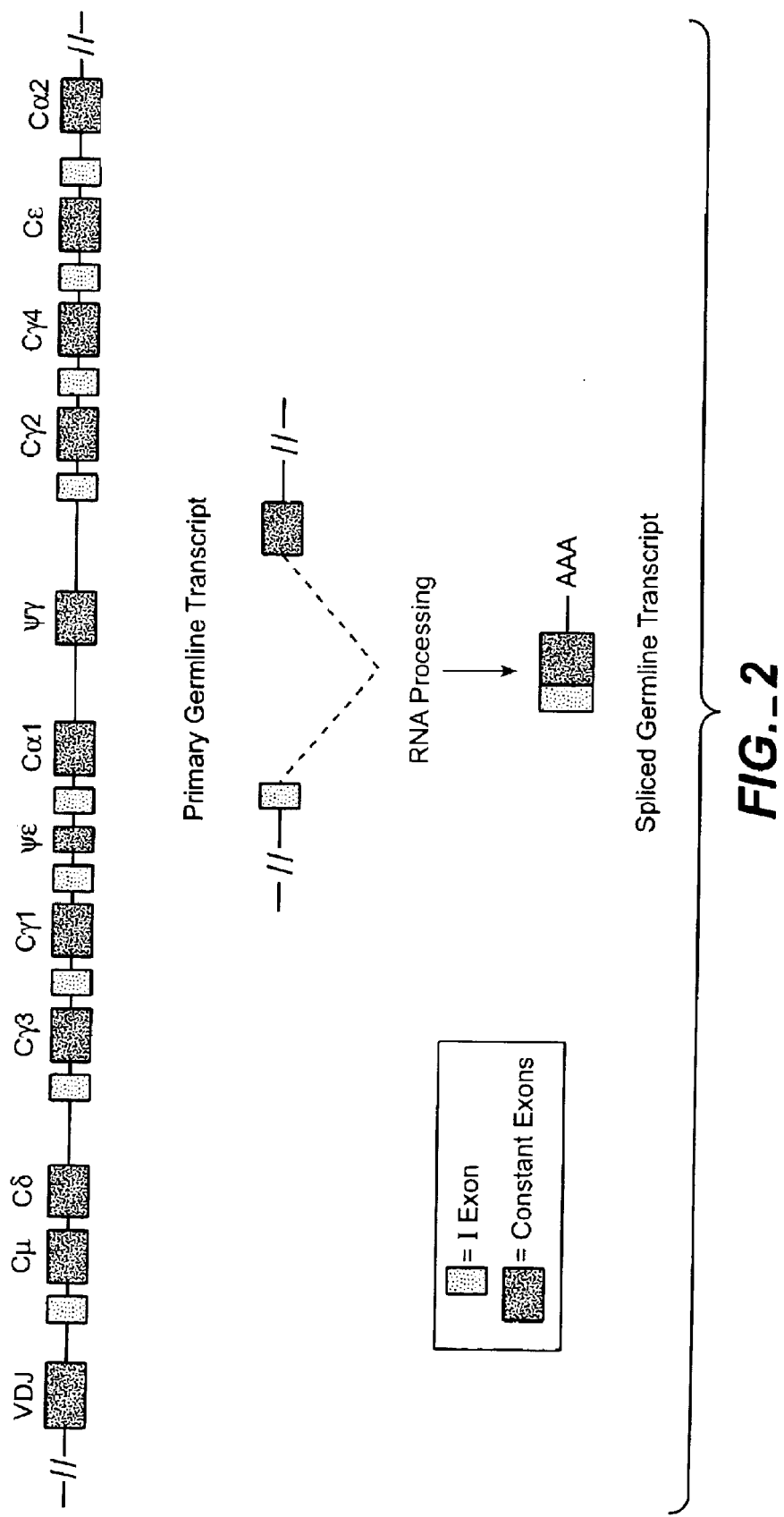
FIG._2

Germline Ig Alpha-2 Probe

CTCTGCTAAGGACAGACGGCCATCAAGGCAGGACCTGGGCCGGCCAGGGCTCCCTCCCACAGCAGCCCTCTTGGCAGG
CAGCCAGACGCCCGTGAGGGTGCCATGGTGGACCTGCCCATGAGGGCCTGCACGCCGGACCTCAGCACTGCGGGCCCTCCA
GCAGCCTGACCACCAGCATCCCCGAGCCTCTTCCCGTGACCCTGAGCCTGACCTGAGCCTGACCGTGACACCCCCAAGATGGGAACGTGGT
CGTCGCATGCCTGGTCCACCTGCCTTCTTCCCCAGGAGCCACTCAGTGTGACCTGTGACCACCAGACCTGGAGCGAACAGAACGGACAGAACGTGACCG
CCAGAAACTTCCCACCTAGCCAGGATGCCTCCGGGACCAGTCCGTGAAGCAGCCAGGAGCCAGCCTGACCCTGCCGGCACACAG
TGCCCAGACGGGCAAGTCCGTGACATGCCACCCCCATGCTGCCACCCCCCGACTGTCGCTGCACCGGACCGGCCC
TCCCCCACCTCCCCATGCTGCCACCCCCCGACTGTCGCTGCACCGGACCGGCCC

Germline Ig Epsilon Probe

GGCTCCACTGCCCGGCACAGAAATAACAACCACGGTTACTGATCATCTGGGAGCTGTCCAGGAACCCGACAGGGAGCCGG
ACGGGCCACACCATCCACAGGACGACCCAAATGGACGACCCGGCGCTTCAGCCTGCTTCAGCCTCCACACAGAGCCCATCCGTCTTCCCCTTG
ACCCGCTGCTGCAAAAACATTCCCTCCAATGCCACCTCCGTG

Germline Ig Gamma 1 Probe

ACACACCAGAGGCTGACTGAGGCCTGAGGCTCCAGGACGACCCGGACTGGGAGCACGAGGAACATGACTGGATGCGGCAGAGCCGGC
CGTGGGGTGATGCCAGGATGCCAGGATGGGCCAGGACCTGAGCTCAGGAGGAGGCAGCAGGGAGCCAGGGCCCCAGGTG
AACGGAGGGGGCTTGTCCAGGCAGCAGGACAGCAGCCTCCACCAAGGACCAGGGTCAGCAGTGCTGGCCGTGGGGCCCCTTCCTCT
CAGCCAGGAGGACAGCCGGCCCTGGGCCTGCCTGGTCAGGACTACATCTCCTCCCGGCTCAAGGACTCTACAGTCCTCCTACACAAGCTCAGAGCTGGG
GGGCACAGCAGCGGCCCTGCACACCTTCCCGGTCAAGGACTACATCTCCTCCTACACGCAGAAGAGCAACGTGGCGGGGAAGAGCTGCTGG
CCAGCGGCGTGCACACCTTCCCGGCTGTCTACACAGTCCTCAGGACTCTACTCCCTCAGTCCTCAGCCGCCTGTCGTGACCTGGTGTCGTGAGCAGTGCCTGAG
AGCAGCTTGGGCACCCAGACCTACATCTGCAACGTGAATCACAAGCCCAGCAACACCAAGGTGGACAAGAAAGTTGAGCC
CAAATCTTGTGACAAAACTCACACATGCCCACCG

FIG._3A

Germline Ig Gamma 2 Probe

CCAAGCCAACAGGGCAGGACACACCAGAGGCCTCGACTGAGGCCTCCATGACGACCAGGCTGGGAGCACGAGGAACATGACG
GGATGCGGCAGAGCCGGCCGTGGGGTGATGCCAGCATGGGCCAGGACCCACCTGAGCTGAGGGCTGAGGAGGCAGTAGAACGAGGAG
GAGGAGGAGGCCCCAGGTGAACGGAGGGGCTTGTCCAGGCAGCAGCCTTGTTGTCCAGGACAGCAGCCTCCTGGTGTCCAGGGCCCATCGGTCTTCCCCTGGCGCTG
GCCGTGGGCCCTCTCCGAGAGCAGCCAGGACAGCAGCCTTCCACCAAGGGCCCATCGGTCTTCCCCTGGCGCCCTGC
TCCAGGAGCACCTCGGCTCTGACCAGCACAGCGGCGTGCACACCTTCCCGGCACACCTTCGGCACACCCTCAGGACTCTTCCCCAGACTCTACTCCCTCAGCAGCG
GAACTCAGGCGCGTGCCCCTCCAGCAACTTCGGCACACCCTCAGACCTACACCGTGCCCTCCAGCAGCTTGGGCACCCAGGAC
TGGTGACCGTGCCCTCCAGCAGCTTGGGCACCCAGGAC
GACAAGACAGTTGAGCGCAAATGTTGTGTCGAGGTGCCACCACCGTCCAGGACCGTCA

Germline Ig Gamma 3 Probe

ACACACCAGAGAGGCTGACTGAGGCCTCCAGGACGACCGGGCTGGGAGCGTGAGGAACATGACGGAGGAACATGGGGCAGAGCCAGC
CATGGGGTGATGCCAGGATGGGCCAGGACCGACCTGAGCTCAGGAGCCAGGACTCAGGGACCCCCAGGTG
AACCGAGGGGCTTGTCCAGGCCGCAGCAGCCTTCCACCAAGGGCCCATCGGTCTTCCCCTGGCCCTCTCT
CAGGCCAGGACAGCAAGGACACAGCCAGCTGCCTGGTCAAGGACTACTTCCCCGAACCGGTGACGGTGTCGTGG
GGGCACAGCGGCGTGCACACCTTCCCGGCTGTGCTACAGTCCTCAGGACTCTACTCCCTCAGCAGCGTGGTGACCGTGCCCTCA
CCAGCGGCGTGCACACCTTCCCAGCAACTCCTCCCAGACTCCCTGAATCAGTGTAATCACCGCAACGCCCAGCGGCAACCGGAGCAAGGTGGACAAGAGAGTTGAGCT
AGCAGCTTGGGCACCCAGACCTACACCGTGAATCCAAGGTGGACAAGAGAGTTGAGCT
CAAAACCCACTTGGTGACAATCTTGTGACACACTCTCCCCGTGCC
CACGGTGCCC

Germline Ig Gamma 4 Probe

GGCCAGCACCACCATGATGGGGAAGCCCAAGCGGAGCGGAGGCCCAGGACCCCAGGCCTTCAGGCACTGATGCCCACCCAGTGC
GAGACGACGGGAGACCGTGGGGCAGGGGCTTCCAAGCACAGCACAGGGCAGGACACAACCAGAGGAGCTGACTGAGGCCTCCAGGACG
ACCCGGCTGGGAGCAGCACGAGGACACACGGGGCAGAACATGACGGAGGGAAACAGGGCAGGCCCCGTGGGGTGATGCCAGGGCTGATGCCAGGAGATGGGCACC
TGAGCTCAGGACCAGGACAGCCTTGTCCAGGACAGCAGCCTTGTGTCCAGGACAGCAGCCTTGTGTCCAGGGATGGCCCGGCAGCATCAC
CAGAGCCCATCTGTGCCTCTTCCCAAGACCAGCCCCAAGGACACAGCCAGCTCCGGCAGTCTCCAGGGCCTCCTGGTGTCAAGGA
GGCCCATCTTCCCGAACCGGTGACGGTGTCCTGGAACTCAGGCGTCCTGGTGACGGTGTCCTGGACCCCCATCCTTCCCGAACCGGTGACGGTGTCCCTGGAACTCAGGCGCCGTGCACACCTTCCCGGCTGTCCTAC
CTACTTCCCGAACCGGTGACGGTGTCCTGGAACTCAGGCGCTGTCCTGGTGACGGTGTCCTGGGAACTGTCCCGAACCGGAGATCCACCTAC
AGTCCTCAGGACTCTACTCCCTCAGCAGCGTGGTGACCGTGCCCTCCAGCAGCCTGGGCACGAAGACCTACACCTGCAACGCACCTAC
GTAGATCACAAGCCCAGCAACACCAAGGTGGACAAGAGAGTTGAGTCCAAATATGGTCCCCCGTC

FIG. 3B

Germline Ig Alpha-1 Probe

GGCCTGGGCCGGGCCAGGGCTCCCCTCCCCACAGCAGCCCTCTCTTGGCAGGCAGCCAGAGACGCCCCGTGAGGGTGGACCTGCCA
TGAGGGCCTGCACGCCGGAGGCCGGCACTCAGCACTGCGGGCCCTCCAGCAGCCTGACCAGCATCCCGACCAGCCCA
AGGTCTTCCCGCTGAGCCTCTGCACCTGTGACCTGGGAGATGGGAACGCCAGCCAGCCTGCCTGCCTGGTCATCGCGGTCCACCGTGAACTTCCCC
CAGGAGCCACTCAGTGTACCACCAGCCTGGAGCGGACAGGGCGTGACCGCCAGGGAAAGCGGACACCCTGCGCCAGAACTTCCCACCACAGCCTC
CGGGGACCTGTACACCACGAGCAGCCAGCTGACCCTGCCCTAGCCGGCCTGCCTAGCCGGCCAAGTCCGTCGACATGCCAC

Germline Ig Alpha-2 Probe

CTCTGCTAAGGACACAGACGGCCATCAAGGCAGGACCCTGGGCCAGGAGGTCTCCCTCCCCACAGCAGCCCTCTTGGCAGG
CAGCCAGAACGCCCGTGAGGGTGGACCTGCCATGAGGGCCTGCCATGGAGGCCGACGCCAGTCAGCACTGCGGGCCCTCCA
GCAGCCTGACCAGCATCCCGAGCCTGACCAGCATCCCCAAGGTCTTCCCGCTGAGCCTCTGCACCACCCCCAAGATGGGAACGTGGT
CGTCGCATGCCTGGTCCAGGGCTTCTCCCCAGGAGCCACTCAGTGTGACCCTGTGTGACACCACGAGCAGCCAGCTGACCG
CCAGAAACTTCCCACCACACTAGCCAGGATGCCTCCGGGGACCTGTACACCACGAGCAGCCAGCTGACCCTGCCGGCCACACAG
TGCCCAGACGGCCAAGTCCGTGACATGCCAC

Germline Ig Epsilon Probe

GGCTCCACTGCCCGGCACAGAAATAACAACCACGGTTACTGATCATCTGGGAGCTGTCCAGGAACCCGACACAGGAGCCGG
ACGGGCCACACCATCCACACACAGCCAAATGGACGACCCGGCGCTTCAGCCTCCACACAGAGCCCATCCGTCTTCCCCTTG
ACCCGCTGCAAAAACATTCCCTCCAATGCCACCACCTCCGTG

Germline Ig Gamma 1 Probe

ACACACCACCAGAGGCTGACTGAGGCCTCCAGGACGACCGGGCTGGGAGCACGAGGAACATGACTGGATGCGGCAGAGCCGGC
CGTGGGGTGATGCCAGGATGGGCACGACGACCTGAGCTCAGGAGGAGCAGAGCCAGGAGCCCCAGGTG
AACGGAGGGGCTTGTCCAGGCCGGCAGCATCACCGGACCCTCCACCAAGGCCACCAAGGCCACCTCCCTGGCCGTGCTGGCCGTGGGGCCCTCCTCT
CAGCCAGGACCAAGGACACAGCAGCCTCCACCAAGGCCACCATCGTCTTCCCCCTGGCCAGTCAGCCCCTGGCACCCTCCTCCAAGAGCACCTCTGG
GGGCACAGCGCCTGGGCTGCCTGGTCGTGAAGGACTACTTCCCCGAACCGG

FIG._4A

Germline Ig Gamma 2 Probe

CCAAGCCAACAGGGCAGGACACACCAGAGGCTGACTGAGGCCTCCATGACGACCAGGCTGGGAGCACGAGGAGAACATGACG
GGATGCGGCAGAGCCGGCCGTGGGGTGATGCCAGCATGGGCAGGACCCACCTGAGCTGCCAGGAGGCAGTAGAACGAGGGAG
GAGGAGAGGCCCCCAGTTGTCTCTGAACGGAGGGCTTGTCCAGGCCAGCATCACTGGAGCCCAGGGCAGGGTCAGCAGTGCTG
GCCGTGGGGCCCTCTCTCCAGGACCAGCAGCCTCCACCAAGGGCCCATCGGTCTTCCCCCTGGCGCCCTGC
TCCAGGAGCACCTGCCCTGGGCTGCCCTGGTCAAGGACTACTTCCCCGAACCGG

Germline Ig Gamma 3 Probe

ACACACCAGAGGCTGACTGAGGCCTCCAGGACGACACCGGGCTGGGAGCGTGAGGAAACATGACGGGATGGGGCAGAGCCAGC
CATGGGGTGATGCCAGGATGGGCCAGCATGACCTGAGCTGCCAGGAGGCAGCAGAGAGGAGGAGAGCAGGCCCCAGGTG
AACCGAGGGGCTTGTCCAGGCCGGCAGCAGCATCACCGAGGGTCAGCAGGGTCAGCAGAGCTGGCCGTAGGGCCCTCCTCT
CAGCCAGGACCAAGGACAGCAGCTTCCTGCCCATCGGTCTTCCCCGCGCCCTGCTCTCCAGGAGCACCTCTGG
GGGCACAGCGGCCTGGGCTGCCCTGGTCAAGGACTACTTCCCCGAACCGGTGACGCGGTGTCGTGTGGAACTCAG

Germline Ig Gamma 4 Probe

GGCCAGCACCACATGGAAGCCCCAAGCGCGGAGCCCAGCAGCCCCAAGCACGGGAGGTGGGCAGCCTTCAGGCACTGATGCCCACCCAGTGC
GAGACGACGGGGACCGTGGGCAGGGCTTCCAAGCCAACAGGCCAGGACACACCAGAGGCTGACTGAGGCCTCCAGGACG
ACCGGGCTGGGGAGCACGAGGACATGACGGGATGCGGCAGAACATGGCCAGGAACCGGTGGGGTGCCAGGCCTGATGGCACGACC
TGAGCTCAGGAGGCCCAGGGCTTGTCCAGGGATGGGGCTTGTCCAGGCCCGGCACGACCAGAGCTCCGGCACGACC
CAGAGCCCAGGGTCAGCAGGGTCAGCAGAGCTGGCCGTAGGGCCGTCCTCTCCGAGAGCAGCACACCCAGGAGCAGCTTCCACCAAG
GGCCCCATCCGTCTTCCCCCTGGCGCCCTGCTCAGGACACAGCCGCCCTGGGCTGCCTGGTCAAGGA
CTACTTCCCCGAACCGG

FIG.__4B

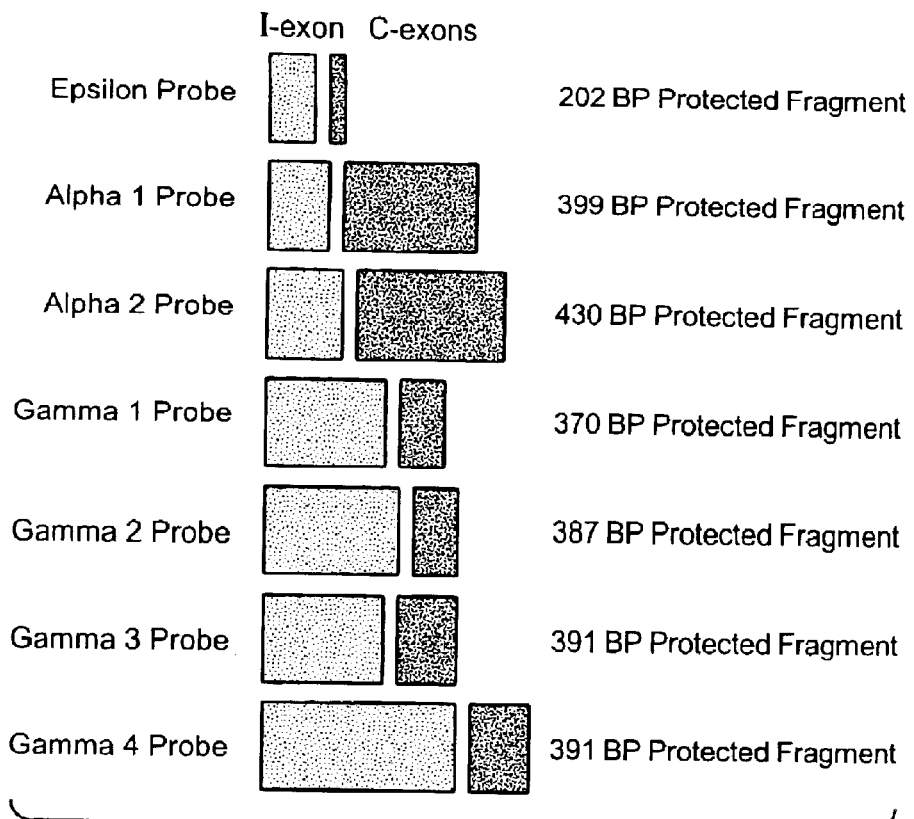
FIG._5
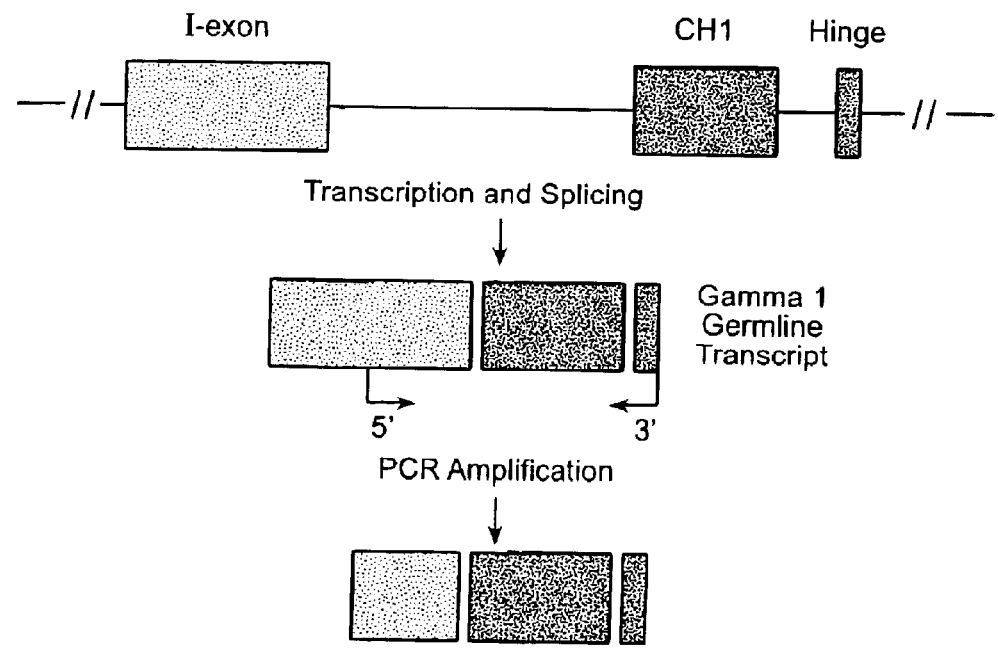
FIG._6

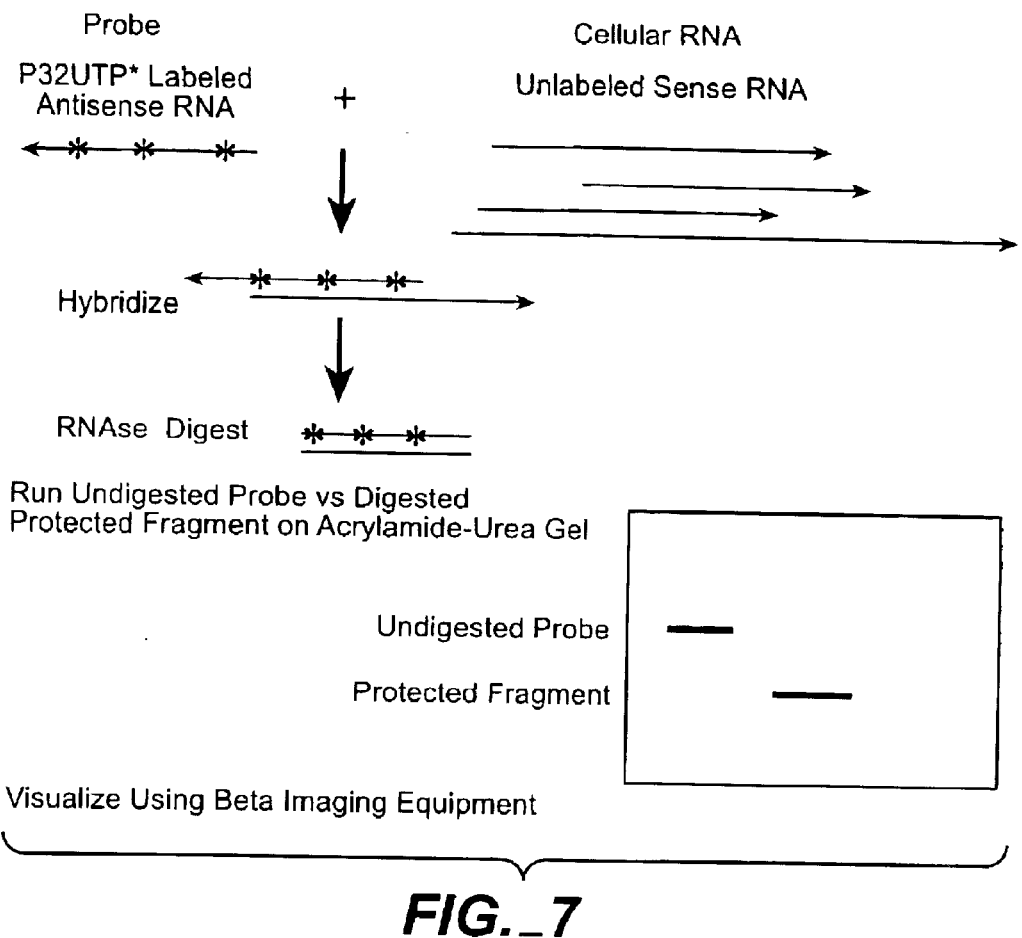
FIG._7
Alpha-1
L04541 = I Region Exon
BC005951 = Constant Region Exons
Alpha-2
L04541 = I Region Exon
AL389978 = Constant Region Exons
Epsilon
X56797 = I Region Exon
J00222 = Constant Region Exons
Gamma-1
A2122127 = I Region Exon
Z17370 = Constant Region Exons
Gamma-2
U39934 = I Region Exon
J00230 = Constant Region Exons
Gamma-3
AI122127 = I Region Exon
X16110 = Constant Region Exons
Gamma-4
X56796 = I Region Exon
K01316 = Constant Region Exons
FIG._9

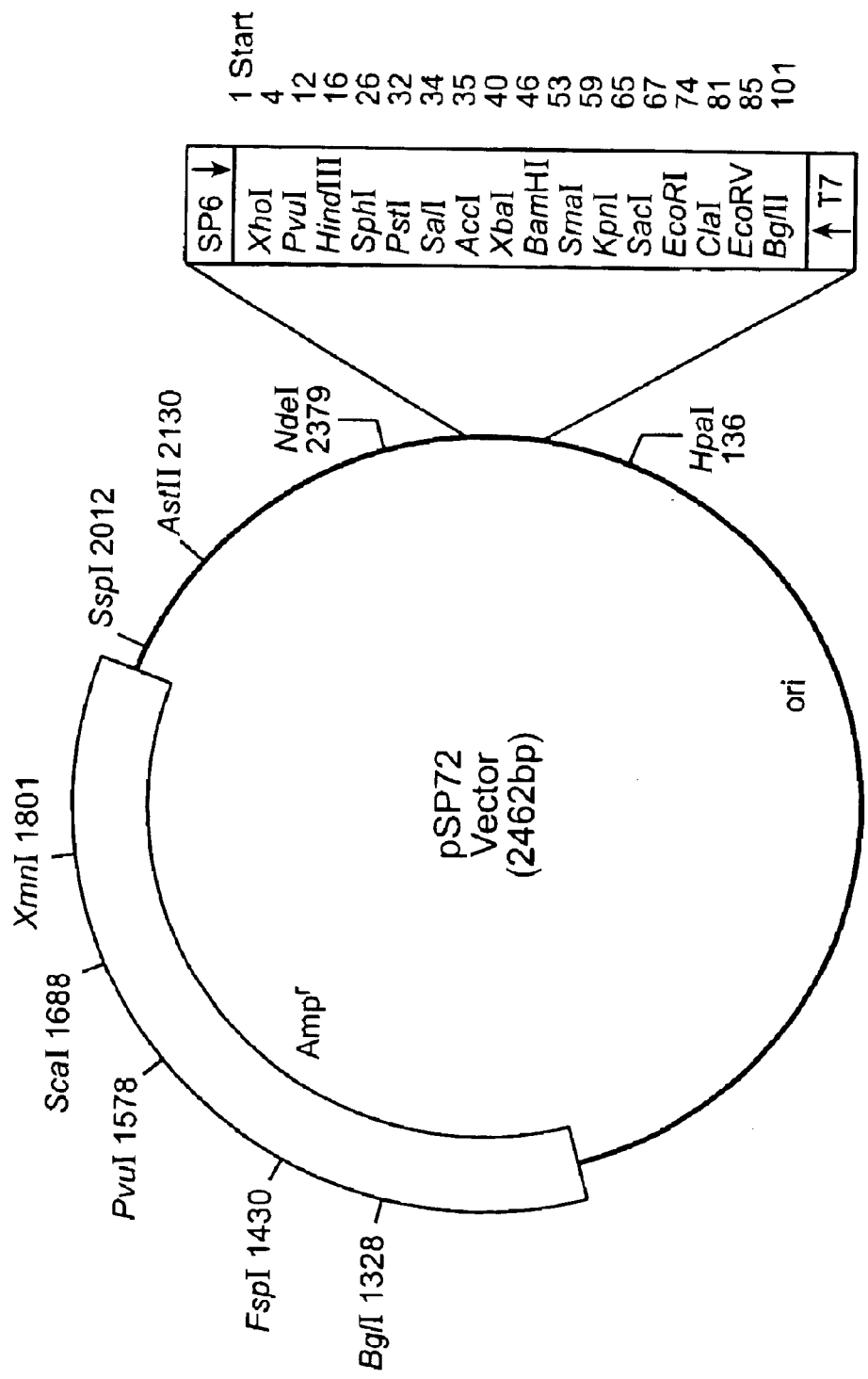
FIG._8

SEQUENCE LISTING

<160> NUMBER OF SEQ ID NOS: 24

<210> SEQ ID NO 1
<211> LENGTH: 533
<212> TYPE: DNA
<213> ORGANISM: Artificial sequence
<220> FEATURE:
<223> OTHER INFORMATION: Germline Ig Alpha-2 probe

<400> SEQUENCE: 1

| | | | | | |
|---|---|---|---|---|---|
| ctctgctaag | gacagacggc | catcaaggca | ggacctgggc | cgggccaggg | ctccctcccc | 60 |
| acagcagccc | tcttggcagg | cagccagacg | cccgtgaggg | tggacctgcc | atgagggcct | 120 |
| gcacgccgga | ggccgcccac | tcagcactgc | gggccctcca | gcagcctgac | cagcatcccc | 180 |
| gaccagcccc | aaggtcttcc | cgctgagcct | cgacagcacc | ccccaagatg | gaacgtggt  | 240 |
| cgtcgcatgc | ctggtccagg | gcttcttccc | ccaggagcca | ctcagtgtga | cctggagcga | 300 |
| aagcggacag | aacgtgaccg | ccagaaactt | cccacctagc | caggatgcct | ccggggacct | 360 |
| gtacaccacg | agcagccagc | tgaccctgcc | ggccacacag | tgcccagacg | gcaagtccgt | 420 |
| gacatgccac | gtgaagcact | acacgaatcc | cagccaggat | gtgactgtgc | cctgcccagt | 480 |
| tccccccacct | cccccatgct | gccacccccg | actgtcgctg | caccgaccgg | ccc        | 533 |

<210> SEQ ID NO 2
<211> LENGTH: 202
<212> TYPE: DNA
<213> ORGANISM: Artificial sequence
<220> FEATURE:
<223> OTHER INFORMATION: Germline Ig Epsilon Probe

<400> SEQUENCE: 2

| | | | | | |
|---|---|---|---|---|---|
| ggctccactg | cccggcacag | aaataacaac | cacggttact | gatcatctgg | gagctgtcca | 60 |
| ggaacccgac | agggagccgg | acgggccaca | ccatccacag | gcaccaaatg | gacgacccgg | 120 |
| cgcttcagcc | tccacacaga | gcccatccgt | cttccccttg | accgctgctg | caaaaacat  | 180 |
| tccctccaat | gccacctccg | tg | | | | 202 |

<210> SEQ ID NO 3
<211> LENGTH: 594
<212> TYPE: DNA
<213> ORGANISM: Artificial sequence
<220> FEATURE:
<223> OTHER INFORMATION: Germline Ig Gamma 1 probe

<400> SEQUENCE: 3

| | | | | | |
|---|---|---|---|---|---|
| acacaccaga | ggctgactga | ggcctccagg | acgaccgggc | tgggagcacg | aggaacatga | 60 |
| ctggatgcgg | cagagccggc | cgtggggtga | tgccaggatg | ggcacgaccg | acctgagctc | 120 |
| aggaggcagc | agagcgaggg | aggaggagag | gccccaggtg | aacggagggg | cttgtccagg | 180 |
| ccggcagcat | caccggagcc | cagggcaggg | tcagcagtgc | tggccgtggg | gccctcctct | 240 |
| cagccaggac | caaggacagc | agcctccacc | aagggcccat | cggtcttccc | cctggcaccc | 300 |
| tcctccaaga | gcacctctgg | gggcacagcg | gccctgggct | gcctggtcaa | ggactacttc | 360 |
| cccgaaccgt | gacggtgtc   | gtggaactca | ggcgccctga | ccagcggcgt | gcacaccttc | 420 |
| ccggctgtcc | tacagtcctc | aggactctac | tccctcagca | gcgtggtgac | cgtgccctcc | 480 |
| agcagcttgg | gcacccagac | ctacatctgc | aacgtgaatc | acaagcccag | caacaccaag | 540 |
| gtggacaaga | aagttgagcc | caaatcttgt | gacaaaactc | acacatgccc | accg        | 594 |

<210> SEQ ID NO 4
<211> LENGTH: 632
<212> TYPE: DNA
<213> ORGANISM: Artificial sequence
<220> FEATURE:
<223> OTHER INFORMATION: Germline Ig Gamma 2 probe

<400> SEQUENCE: 4

| | | | | | |
|---|---|---|---|---|---|
| ccaagccaac | agggcaggac | acaccagagg | ctgactgagg | cctccatgac | gaccaggctg | 60 |
| ggagcacgag | gaacatgacg | ggatgcggca | gagccggccg | tggggtgatg | ccagcatggg | 120 |
| caggacccac | ctgagctgag | gaggcagtag | aacgagggag | gaggagaggc | cccaggtgaa | 180 |
| cggaggggct | tgtccaggcc | agcagcatca | ctggagccca | gggcagggtc | agcagtgctg | 240 |
| gccgtggggc | cctctctcag | ccaggaccaa | ggacagcagc | ctccaccaag | ggcccatcgg | 300 |
| tcttccccct | ggcgccctgc | tccaggagca | cctccgagag | cacagcggcc | ctgggctgcc | 360 |
| tggtcaagga | ctacttcccc | gaaccggtga | cggtgtcgtg | gaactcaggc | gctctgacca | 420 |
| gcggcgtgca | caccttccca | gctgtcctac | agtcctcagg | actctactcc | ctcagcagcg | 480 |
| tggtgaccgt | gccctccagc | aacttcggca | cccagaccta | cacctgcaac | gtagatcaca | 540 |
| agcccagcaa | caccaaggtg | gacaagacag | ttgagcgcaa | atgttgtgtc | gagtgcccac | 600 |
| cgtgcccagc | accacctgtg | gcaggaccgt | ca | | | 632 |

<210> SEQ ID NO 5
<211> LENGTH: 650
<212> TYPE: DNA
<213> ORGANISM: Artificial sequence
<220> FEATURE:
<223> OTHER INFORMATION: Germline Ig Gamma 3 probe

<400> SEQUENCE: 5

| | | | | | |
|---|---|---|---|---|---|
| acacaccaga | ggctgactga | ggcctccagg | acgaccgggc | tgggagcgtg | aggaacatga | 60 |
| cgggatgggg | cagagccagc | catggggtga | tgccaggatg | gcatgaccg | acctgagctc | 120 |
| aggaggcagc | agagagaggg | aggaggagag | gccccaggtg | aaccgagggg | cttgtccagg | 180 |
| ccggcagcat | caccggagcc | cagggcaggg | tcagcagagc | tggccgtagg | gccctcctct | 240 |
| cagccaggac | caaggacagc | agcttccacc | aagggcccat | cggtcttccc | cctggcgccc | 300 |
| tgctccagga | gcacctctgg | gggcacagcg | gccctgggct | gcctggtcaa | ggactacttc | 360 |
| cccgaaccgg | tgacggtgtc | gtggaactca | ggcgccctga | ccagcggcgt | gcacaccttc | 420 |
| ccggctgtcc | tacagtcctc | aggactctac | tccctcagca | gcgtggtgac | cgtgccctcc | 480 |
| agcagcttgg | gcacccagac | ctacacctgc | aacgtgaatc | acaagcccag | caacaccaag | 540 |
| gtggacaaga | gagttgagct | caaaaccccca | cttggtgaca | caactcacac | atgcccacgg | 600 |
| tgcccagagc | ccaaatcttg | tgacacacct | cccccgtgcc | cacggtgccc | | 650 |

<210> SEQ ID NO 6
<211> LENGTH: 705
<212> TYPE: DNA
<213> ORGANISM: Artificial sequence
<220> FEATURE:
<223> OTHER INFORMATION: Germline Ig Gamma 4 probe

<400> SEQUENCE: 6

| | | | | | |
|---|---|---|---|---|---|
| ggccagcacc | acatggaagc | ccaagcggag | ccagcacggg | ggaggtgggc | agccttcagg | 60 |
| cactgatgcc | cacccagtgc | gagacgacgg | ggaccgtggg | caggggcttc | caagccaaca | 120 |

| | |
|---|---|
| gggcaggaca caccagaggc tgactgaggc ctccaggacg accgggctgg gagcacgagg | 180 |
| aacatgacgg gatgcggcag aaccggccgt ggggtgatgc caggatgggc acgaccgacc | 240 |
| tgagctcagg aggcagcaga gcgagggagg aggagaggcc ccaggtgaac ggagggcttt | 300 |
| gtccaggccg gcagcatcac cagagcccag ggcagggtca gcagagctgg ccgtagggcc | 360 |
| ctcctctcag ccaggaccaa ggacagcagc ttccaccaag ggcccatccg tcttcccct | 420 |
| ggcgccctgc tccaggagca cctccgagag cacagccgcc tgggctgcc tggtcaagga | 480 |
| ctacttcccc gaaccggtga cggtgtcgtg gaactcaggc gccctgacca gcggcgtgca | 540 |
| caccttcccg gctgtcctac agtcctcagg actctactcc ctcagcagcg tggtgaccgt | 600 |
| gccctccagc agcttgggca cgaagaccta cacctgcaac gtagatcaca agcccagcaa | 660 |
| caccaaggtg gacaagagag ttgagtccaa atatggtccc ccgtc | 705 |

<210> SEQ ID NO 7
<211> LENGTH: 399
<212> TYPE: DNA
<213> ORGANISM: Artificial sequence
<220> FEATURE:
<223> OTHER INFORMATION: Germline Ig Alpha-1 proble

<400> SEQUENCE: 7

| | |
|---|---|
| ggcctgggcc gggccagggc tccctcccca cagcagccct cttggcaggc agccagacgc | 60 |
| ccgtgagggt ggacctgcca tgagggcctg cacgccggag gccgcccact cagcactgcg | 120 |
| ggccctccag cagcctgacc agcatccccg accagcccca aggtcttccc gctgagcctc | 180 |
| tgcagcaccc agccagatgg gaacgtggtc atcgcctgcc tggtccaggg cttcttcccc | 240 |
| caggagccac tcagtgtgac ctggagcgaa agcggacagg gcgtgaccgc cagaaacttc | 300 |
| ccacccagcc aggatgcctc cggggacctg tacaccacga gcagccagct gaccctgccg | 360 |
| gccacacagt gcctagccgg caagtccgtg acatgccac | 399 |

<210> SEQ ID NO 8
<211> LENGTH: 430
<212> TYPE: DNA
<213> ORGANISM: Artificial sequence
<220> FEATURE:
<223> OTHER INFORMATION: Germline Ig Alpha-2 probe

<400> SEQUENCE: 8

| | |
|---|---|
| ctctgctaag gacagacggc catcaaggca ggacctgggc cgggccaggg ctccctcccc | 60 |
| acagcagccc tcttggcagg cagccagacg cccgtgaggg tggacctgcc atgagggcct | 120 |
| gcacgccgga ggccgcccac tcagcactgc gggccctcca gcagcctgac cagcatcccc | 180 |
| gaccagcccc aaggtcttcc cgctgagcct cgacagcacc cccaagatg ggaacgtggt | 240 |
| cgtcgcatgc ctggtccagg gcttcttccc ccaggagcca ctcagtgtga cctggagcga | 300 |
| aagcggacag aacgtgaccg ccagaaactt cccacccagc caggatgcct ccggggacct | 360 |
| gtacaccacg agcagccagc tgaccctgcc ggccacacag tgcccagacg caagtccgt | 420 |
| gacatgccac | 430 |

<210> SEQ ID NO 9
<211> LENGTH: 202
<212> TYPE: DNA
<213> ORGANISM: Artificial sequence
<220> FEATURE:
<223> OTHER INFORMATION: Germline Ig Epsilon probe

<400> SEQUENCE: 9

```
ggctccactg cccggcacag aaataacaac cacggttact gatcatctgg gagctgtcca      60
ggaacccgac agggagccgg acgggccaca ccatccacag gcaccaaatg gacgacccgg     120
cgcttcagcc tccacacaga gcccatccgt cttcccttg acccgctgct gcaaaaacat      180
tccctccaat gccacctccg tg                                              202

<210> SEQ ID NO 10
<211> LENGTH: 370
<212> TYPE: DNA
<213> ORGANISM: Artificial sequence
<220> FEATURE:
<223> OTHER INFORMATION: Germline Ig Gamma 1 probe

<400> SEQUENCE: 10
acacaccaga ggctgactga ggcctccagg acgaccgggc tgggagcacg aggaacatga      60
ctggatgcgg cagagccggc cgtggggtga tgccaggatg gcacgaccg acctgagctc     120 aggaggcagc agagcgaggg aggaggagag gccccaggtg aacggagggg cttgtccagg     180
ccggcagcat caccggagcc cagggcaggg tcagcagtgc tggccgtggg gccctcctct     240
cagccaggac caaggacagc agcctccacc aagggcccat cggtcttccc cctggcaccc     300
tcctccaaga gcacctctgg gggcacagcg ccctgggct gcctggtcaa ggactacttc      360
cccgaaccgg                                                            370

<210> SEQ ID NO 11
<211> LENGTH: 387
<212> TYPE: DNA
<213> ORGANISM: Artificial sequence
<220> FEATURE:
<223> OTHER INFORMATION: Germline Ig Gamma 2 proble

<400> SEQUENCE: 11
ccaagccaac agggcaggac acaccagagg ctgactgagg cctccatgac gaccaggctg      60
ggagcacgag gaacatgacg ggatgcggca gagccggccg tggggtgatg ccagcatggg     120
caggacccac ctgagctgag gaggcagtag aacgagggga gggagaggc cccaggtgaa      180 cggaggggct tgtccaggcc agcagcatca ctggagccca gggcagggtc agcagtgctg     240
gccgtggggc cctctctcag ccaggaccaa ggacagcagc ctccaccaag ggcccatcgg     300
tcttccccct ggcgccctgc tccaggagca cctccgagag cacagcggcc ctgggctgcc     360
tggtcaagga ctacttcccc gaaccgg                                         387

<210> SEQ ID NO 12
<211> LENGTH: 391
<212> TYPE: DNA
<213> ORGANISM: Artificial sequence
<220> FEATURE:
<223> OTHER INFORMATION: Germline Ig Gamma 3 probe

<400> SEQUENCE: 12
acacaccaga ggctgactga ggcctccagg acgaccgggc tgggagcgtg aggaacatga      60
cgggatgggg cagagccagc catggggtga tgccaggatg gcatgaccg acctgagctc     120 aggaggcagc agagagaggg aggaggagag gccccaggtg aaccgagggg cttgtccagg     180
ccggcagcat caccggagcc cagggcaggg tcagcagagc tggccgtagg gccctcctct     240
cagccaggac caaggacagc agcttccacc aagggcccat cggtcttccc cctggcgccc     300
tgctccagga gcacctctgg gggcacagcg ccctgggct gcctggtcaa ggactacttc      360
```

```
cccgaaccgg tgacggtgtc gtggaactca g                              391
```

<210> SEQ ID NO 13
<211> LENGTH: 497
<212> TYPE: DNA
<213> ORGANISM: Artificial sequence
<220> FEATURE:
<223> OTHER INFORMATION: Germline Ig Gamma 4 probe

<400> SEQUENCE: 13

```
ggccagcacc acatggaagc ccaagcggag ccagcacggg ggaggtgggc agccttcagg    60
cactgatgcc cacccagtgc gagacgacgg ggaccgtggg caggggcttc caagccaaca   120
gggcaggaca caccagaggc tgactgaggc ctccaggacg accgggctgg gagcacgagg   180
aacatgacgg gatgcggcag aaccggccgt ggggtgatgc caggatgggc acgaccgacc   240
tgagctcagg aggcagcaga gcgagggagg aggagaggcc ccaggtgaac ggagggcttt   300
gtccaggccg gcagcatcac cagagcccag ggcagggtca gcagagctgg ccgtagggcc   360
ctcctctcag ccaggaccaa ggacagcagc ttccaccaag ggcccatccg tcttccccct   420
ggcgccctgc tccaggagca cctccgagag cacagccgcc ctgggctgcc tggtcaagga   480
ctacttcccc gaaccgg                                                  497
```

<210> SEQ ID NO 14
<211> LENGTH: 61
<212> TYPE: PRT
<213> ORGANISM: Artificial sequence
<220> FEATURE:
<223> OTHER INFORMATION: preferred coiled-coil presentation structure

<400> SEQUENCE: 14

```
Met Gly Cys Ala Ala Leu Glu Ser Glu Val Ser Ala Leu Glu Ser Glu
  1               5                  10                  15

Val Ala Ser Leu Glu Ser Glu Val Ala Ala Leu Gly Arg Gly Asp Met
             20                  25                  30

Pro Leu Ala Ala Val Lys Ser Lys Leu Ser Ala Val Lys Ser Lys Leu
         35                  40                  45

Ala Ser Val Lys Ser Lys Leu Ala Ala Cys Gly Pro Pro
     50                  55                  60
```

<210> SEQ ID NO 15
<211> LENGTH: 6
<212> TYPE: PRT
<213> ORGANISM: Artificial sequence
<220> FEATURE:
<223> OTHER INFORMATION: loop structure

<400> SEQUENCE: 15

```
Gly Arg Gly Asp Met Pro
  1               5
```

<210> SEQ ID NO 16
<211> LENGTH: 69
<212> TYPE: PRT
<213> ORGANISM: Artificial sequence
<220> FEATURE:
<223> OTHER INFORMATION: preferred minobody presentation structure

<400> SEQUENCE: 16

```
Met Gly Arg Asn Ser Gln Ala Thr Ser Gly Phe Thr Phe Ser His Phe
  1               5                  10                  15
```

Tyr Met Glu Trp Val Arg Gly Gly Glu Tyr Ile Ala Ala Ser Arg His
                20                  25                  30

Lys His Asn Lys Tyr Thr Thr Glu Tyr Ser Ala Ser Val Lys Gly Arg
        35                  40                  45

Tyr Ile Val Ser Arg Asp Thr Ser Gln Ser Ile Leu Tyr Leu Gln Lys
    50                  55                  60

Lys Lys Gly Pro Pro
65

<210> SEQ ID NO 17
<211> LENGTH: 7
<212> TYPE: PRT
<213> ORGANISM: Simian virus 40

<400> SEQUENCE: 17

Pro Lys Lys Lys Arg Lys Val
1               5

<210> SEQ ID NO 18
<211> LENGTH: 6
<212> TYPE: PRT
<213> ORGANISM: Homo sapiens

<400> SEQUENCE: 18

Ala Arg Arg Arg Arg Pro
1               5

<210> SEQ ID NO 19
<211> LENGTH: 10
<212> TYPE: PRT
<213> ORGANISM: Mus musculus

<400> SEQUENCE: 19

Glu Glu Val Gln Arg Lys Arg Gln Lys Leu
1               5                   10

<210> SEQ ID NO 20
<211> LENGTH: 9
<212> TYPE: PRT
<213> ORGANISM: Mus musculus

<400> SEQUENCE: 20

Glu Glu Lys Arg Lys Arg Thr Tyr Glu
1               5

<210> SEQ ID NO 21
<211> LENGTH: 20
<212> TYPE: PRT
<213> ORGANISM: Xenopus laevis

<400> SEQUENCE: 21

Ala Val Lys Arg Pro Ala Ala Thr Lys Lys Ala Gly Gln Ala Lys Lys
1               5                   10                  15

Lys Lys Leu Asp
            20

<210> SEQ ID NO 22
<211> LENGTH: 10
<212> TYPE: PRT
<213> ORGANISM: Artificial sequence
<220> FEATURE:
<223> OTHER INFORMATION: preferred stability sequence
<221> NAME/KEY: MISC_FEATURE

```
-continued

<222> LOCATION: (3)..(6)
<223> OTHER INFORMATION: "Xaa" at positions 3 to 6 can be any amino acid

<400> SEQUENCE: 22

Met Gly Xaa Xaa Xaa Xaa Gly Gly Pro Pro
1               5                   10

<210> SEQ ID NO 23
<211> LENGTH: 5
<212> TYPE: PRT
<213> ORGANISM: Artificial sequence
<220> FEATURE:
<223> OTHER INFORMATION: linker consensus sequence

<400> SEQUENCE: 23

Gly Ser Gly Gly Ser
1               5

<210> SEQ ID NO 24
<211> LENGTH: 4
<212> TYPE: PRT
<213> ORGANISM: Artificial sequence
<220> FEATURE:
<223> OTHER INFORMATION: linker consensus sequence

<400> SEQUENCE: 24

Gly Gly Gly Ser
1
```

RNASE PROBE PROTECTION ASSAYS IN SCREENING FOR MODULATORS OF IMMUNOGLOBULIN GERMLINE TRANSCRIPTION

This application is a continuing application of U.S. provisional patent application Ser. No. 60/201,333, filed 2 May 2000.

BACKGROUND OF THE INVENTION

Immunoglobulins must bind to a vast array of foreign molecules and thus exist in many forms. The sequence of the variable (V) region of immunoglobulin molecules varies tremendously, conferring virtually unlimited capacity to bind antigens. The constant (C) region comes in five different varieties: $\alpha$, $\delta$, $\epsilon$, $\gamma$ and $\mu$, providing five different isotypes: IgA, IgD, IgE, IgG and IgM, each of which performs a different set of functions. B cells initially produce only IgM and IgD, and must be activated or induced to produce the other isoforms, such as IgE.

The course of IgE production starts with the activation of B cells. Upon activation with an antigen, B cells follow one of two differentiation pathways: they may differentiate directly into plasma cells, which are basically antibody-secreting factories, or they may give rise to germinal centers, specialized structures within lymphoid organs. In the latter, successive rounds of mutation of the V region genes is followed by expression of the gene products on the cell surface, with selection of the cells on the basis of the affinity of the mutated immunoglobulins against the antigen.

In both pathways of antigen-induced B cell differentiation, isotype switching occurs in which the C region of the immunoglobulin heavy chain changes from the joint expression of IgM and IgD on naive B cells to expression of one of the downstream isotypes such as IgE. This switching involves the replacement of upstream C regions with a downstream C region that has biologically distinct effector functions without changing the structure of the variable portion and, hence, its specificity. For IgE switching, a deletional rearrangement of the Ig heavy chain gene locus occurs, a rearrangement that joins the switch region of the $\mu$ gene, S$\mu$, with the corresponding region of the $\epsilon$ gene, S$\epsilon$. This switching is minimally induced by IL-4 or IL-13, which initiates transcription through the S$\epsilon$ region, resulting in the synthesis of germ-line (or "sterile") $\epsilon$ transcripts; that is, transcripts of the unrearranged C$\epsilon$ heavy genes. This IL-4 induced transcription is inhibited by IFN-$\gamma$, IFN$\alpha$, and TGF-$\beta$. A second signal, normally delivered by T cells, is required for actual switch recombination leading to IgE production. The T cell signal may be replaced by monoclonal antibodies to CD40, Epstein-Barr viral infection, or hydrocortisone.

Recently, the mechanism of class switch recombination has been explained by an accessibility model, wherein the specificity of the switch gene rearrangement is determined by the modulation of switch region accessibility; that is, the opening up of the chromatin in certain areas, allowing the required protein/enzyme complexes access to the genes.

IgE antibodies are crucial immune mediators of allergic reactions, and have been shown to be responsible for the induction and maintenance of allergic symptoms. For example, the introduction of anti-IgE antibodies has been shown to interfere with IgE function, thus working to alleviate allergic symptoms. See Jardieu, Current Op. Immunol. 7:779–782 (1995), Shields et al., Int. Arch. Allergy. Immunol. 107:308–312 (1995).

The expression of germline transcripts has been shown to precede and be essential for immunoglobulin or antibody class switch recombination in differentiating B cells. As B cells proceed from the expression of Immunoglobulin Mu (IgM) and Delta (IgD) to the downstream forms of Ig, cytokine signals help determine which germline transcripts will be produced and thus which constant region will recombine with the variable region of the expressed Ig. For example, IL-4 has been shown to induce the expression of IgE germline transcript and TGF$\beta$1 can induce IgA.

RNAse protection assays (RPAs) are described in Berton et al, PNAS USA 86:2829 (1989); Berton et al., Int. Immunol. 4:387 (1992); Turaga et al., J. Immunol. 151:1383 (1993); and Warren et al., J. Immunol. 155:5637 (1995), all of which are expressly incorporated by reference;

It is one object of the present invention to use RNAse protection assays to screen and evaluate candidate agents for the ability to effect one or more germline transcripts. In addition, it is an object of the invention to provide for specific RNAse protection probes (RPPs) that can be used to facilitate this identification. Furthermore, it is an object of the invention to provide kits and compositions for these assays and analyses.

SUMMARY OF THE INVENTION

In accordance with the above objects, the present invention provides methods of screening for candidate agents capable of modulating germline transcription comprising adding a library of candidate agents to a plurality of cells and preparing mRNA from said plurality of cells to form an mRNA mixture. At least a first RNAse protection probe (RPP) substantially complementary to a first germline mRNA is added to the mixture to form a first hybridization complex between the first germline mRNA and the first RPP. An RNAse protection enzyme (RPE) is added to the mixture, such that mRNA that is not protected is digested. The amount of the first germline mRNA is quantified as compared to a cell in the absence of a candidate agent. Optionally, at least one bioactive agent that alters the amount of the first germline mRNA is identified and characterized.

In a further aspect, the invention further comprises adding to the mixture at least a second RNAse protection probe (RPP) substantially complementary to a second germline mRNA to form a second hybridization complex, and quantifying the amount of said second germline mRNA as compared to a cell in the absence of a candidate agent. At least one bioactve agent is identified that alters the amount of the first germline mRNA but not the second germline mRNA.

In an additional aspect, the present invention provides methods of quantifying the amount of a plurality of germline constructs comprising preparing mRNA from the plurality of cells to form an mRNA mixture, and adding at least three RNAse protection probes (RPPs) selected from the group consisting of the sequences depicted in FIGS. 3A–3B or 4A–4B (SEQ ID NOS:1–13). An RNAse protection enzyme (RPE) is added to the mixture, such that mRNA that is not protected is digested, and the amount of each germline mRNA is quantified.

DETAILED DESCRIPTION OF THE DRAWINGS

FIG. 1 depicts the general mechanism of germline transcription and IgE switching.

FIG. 2 depicts the human chromosome 14 heavy chain gene map.

FIGS. 3A–3B (SEQ ID NOS:1–6) depict the sequences of some "long" RPPs of the invention, these probes being directed to human immunoglobulin germline transcripts.

FIGS. 4A–4B (SEQ ID NOS:7–13) depict the sequences of some "short" RPPs of the invention, these probes being directed to human immunoglobulin germline transcripts.

FIG. 5 depicts a schematic of the RPPs of the invention.

FIG. 6 depicts a schematic of the IgG1 probe.

FIG. 7 depicts a schematic of the RNAse protection assay itself.

FIG. 8 depicts a commercially available vector for the production of the RPPs of the invention. The vector circle map of the pSP72 Vector (Promega, Madison, Wis.) shows the following sequence reference points:

a. SP6 RNA polymerase transcription initiation site at position 1.
b. T7 RNA polymerase transcription site at position 101.
c. SP6 RNA polymerase promoter from position 2446 to position 6.
d. 77 RNA polymerase promoter from position 2446 to position 6.
e. multiple cloning sites from position 4 to position 90.
f. β-lactamase (Amp') coding region from position 1135 to position 1995.

The vector is capable of use for transcription in vitro from dual opposed promoters, using the protocol from the Riboprobe® in vitro Transcritpion Systems Technical Manual (# TM061; Promega, Madison, Wis.). The pSP72 and pSP73 vectors are identical except for the orientation of the multiple cloning region.

FIG. 9 lists the Genbank accession numbers at which nucleic acid sequences used to design the present RPA probes are found. The figure also depicts which portion of the respective Ig gene the nucleic acid sequences found at the accession numbers correspond to.

DETAILED DESCRIPTION OF THE INVENTION

In the present invention, RNAse probe protection assays (RPA) are used to detect and quantify specific germline mRNAs even at very low abundance relative to internal housekeeping standards within the same sample of RNA. RNAse protection assays are based on the addition of labeled antisense RNAse protection probes (RPPs; also referred to as RNAse protection assay (RPA) probes) to mRNA populations. If the RPP comprises sufficient complementarity to the germline mRNA, the two will form a hybridization complex. The addition of RNAse protection enzymes, e.g. enzymes that digest single stranded RNA but do not digest double stranded nucleic acids, allows the removal or digestion of any mRNA that does not correspond to the probe sequences. The germline transcript can then be quantified and evaluated, for example through the determination and quantitation of protected RPP (either in a single stranded form, e.g. after denaturation of the hybridization complex, or as a hybridization complex). This allows for screening for candidate agents capable of modulating germline transcription (such candidate agents sometimes referred to herein as "modulators").

Message levels in different samples can be quantified relative to each other by normalizing amounts of mRNA and further normalizing to the level of RNAse protected transcripts of "housekeeping genes" between samples. Specific probes are amplified and cloned that hybridize to the human germline transcripts of IgE, IgS1, IgA2, IgG1, IgG2, IgG3 and IgG4. Whole animals, cell cultures from primary tissue, or established cell lines can be treated with candidate agents (including, but not limited to, peptides, small molecules, cDNAs, cytokines or other modifiers or modulators) and the extracted RNA can be examined using the RPA probes for expression of germline transcripts. A particular advantage to the present invention is the ability to test for modulators of human germline transcript production.

Accordingly, the present invention provides methods of screening for candidate agents capable of modulating germline transcription. By "modulate" herein is meant an increase in activity, a decrease in activity, or a change in the type or kind of activity present. Thus, such candidate agent modulators of germline transcription include molecules that will either inhibit all or some germline transcription or the amount of transcript present, of a single germline transcript or a plurality of them, as well as molecules that will increase the quantity of germline transcripts or transcription, of a single germline transcript or a plurality of them, as well as molecules that will alter the ratio of the different germline transcripts in a cell relative to a cell that did not get exposed to the candidate agent Particularly preferred in some embodiments are inhibitors of germline transcripts, particularly IgE transcripts. Additionally preferred are inhibitors of IgE transcripts that do not inhibit IgA and/or IgG transcripts.

The methods comprise adding at least one, and preferably a library of candidate agents, to a plurality of cells. By a "population of cells" or "library of cells" herein is meant at least two cells, with at least about $10^3$ being preferred, at least about $10^5$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line. In a preferred embodiment, cells that are replicating or proliferating are used; this may allow the use of retroviral vectors for the introduction of peptide or nucleic acid candidate bioactive agents. Alternatively, non-replicating cells may be used, and other vectors (such as adenovirus and lentivirus vectors) can be used. In addition, although not required, the cells are compatible with dyes and antibodies. Preferred cell types for use in the invention include, but are not limited to, mammalian cells, including animal (rodents, including mice, rats, hamsters and gerbils), primates, and human cells, particularly including tumor cells of all types, including breast, skin, lung, cervix, colonrectal, leukemia, brain, etc.

In one embodiment, the cells are primary cells from a patient sample, particularly a human sample. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples; purified samples; raw samples (bacteria, virus, genomic DNA, etc.; as will be appreciated by those in the art, virtually any experimental manipulation may have been done on the sample.

A library of candidate agents is introduced into the cells. The term "candidate bioactive agent" or "exogenous compound" as used herein describes any molecule, e.g., protein, oligopeptide, small organic molecule, polysaccharide, polynucleotide, etc. that can be screened for activity as outlined herein. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Particularly preferred are small organic compounds having a molecular weight of more than 100 and less than about 2,000 daltons, more preferably less than about 1500 daltons, more preferably less than about 1000 daltons, more preferably less than 500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "proteins" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine; citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occuring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, as is more fully outlined below, the candidate agents are either randomized proteins (including biased proteins or proteins with fusion partners) or expression products of cDNA libraries or libraries derived from cDNA libraries, such as fragmented (including randomly fragmented cDNA libraries). These are added to the cells as nucleic acids encoding these proteins.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566(1993); Carisson, et a l., Nature, 380:207 (199), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al. J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in antisense Research", Ed. Y.

S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al. Chem. Soc. Rev., (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occuring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eucaryotic genomes or cDNA libraries may be used as is outlined above for proteins.

In a preferred embodiment, the candidate bioactive agents are organic chemical moieties, a wide variety of which are available in the literature.

In a preferred embodiment, a library of different candidate bio active agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10_9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^5$, preferably at least $10^7$, more preferably at least $10^5$ and most preferably at least $10^9$ different sequences are simultaneously analyzed in the subject methods. Preferred methods maximize library size and diversity.

The candidate bioactive agents are combined or added to a cell or population of cells. Suitable cell types for different embodiments are outlined above.

The candidate bioactive agent and the cells are combined. As will be appreciated by those in the art, this may accomplished in any number of ways, including adding the candidate agents to the surface of the cells, to the media containing the cells, or to a surface on which the cells are growing or in contact with; adding the agents into the cells, for example by using vectors that will introduce the agents into the cells (i.e. when the agents are nucleic acids or proteins).

In a preferred embodiment, the candidate bioactive agents are either nucleic acids or proteins (proteins in this context includes proteins, oligopeptides, and peptides) that are introduced into the host cells using retroviral vectors, as is generally outlined in PCT US97/01019 and PCT US97/01048, both of which are expressly incorporated by reference. Generally, a library of retroviral vectors is made using retroviral packaging cell lines that are helper-defective and are capable of producing all the necessary trans proteins, including gag, pol and env, and RNA molecules that have in cis the $\Psi$ packaging signal. Briefly, the library is generated in a retrovirus DNA construct backbone; standard oligonucleotide synthesis is done to generate either the candidate agent or nucleic acid encoding a protein, for example a random peptide, using techniques well known in the art. After generation of the DNA library, the library is cloned into a first primer. The first primer serves as a "cassette", which is inserted into the retroviral construct. The first primer generally contains a number of elements, including for example, the required regulatory sequences (e.g. translation, transcription, promoters, etc), fusion partners, restriction endonuclease (cloning and subcloning) sites, stop codons (preferably in all three frames), regions of complementarity for second strand priming (preferably at the end of the stop codon region as minor deletions or insertions may occur in the random region), etc.

A second primer is then added, which generally consists of some or all of the complementarity region to prime the first primer and optional necessary sequences for a second unique restriction site for subcloning. DNA polymerase is added to make double-stranded oligonucleotides. The double-stranded oligonucleotides are cleaved with the appropriate subcloning restriction endonucleases and subcloned into the target retroviral vectors, described below.

Any number of suitable retroviral vectors may be used. Generally, the retroviral vectors may include: selectable marker genes under the control of internal ribosome entry sites (IRES) that greatly facilitates the selection of cells expressing peptides at uniformly high levels; and promoters driving expression of a second gene, placed in sense or anti-sense relative to the 5' LTR. Suitable selection genes include, but are not limited to, neomycin, blastocidin, bleomycin, puromycin, and hygromycin resistance genes, as well as self-fluorescent markers such as green fluorescent protein, enzymatic markers such as lacZ, and surface proteins such as CD8, etc.

Preferred vectors include a vector based on the murine stem cell virus (MSCV) (see Hawley et al., Gene Therapy 1:136 (1994)) and a modified MFG virus (Rivere et al., Genetics 92:6733 (1995)), and pBABE, outlined in the examples.

The retroviruses may include inducible and constitutive promoters for the expression of the candidate agent. For example, there are situations wherein it is necessary to induce peptide expression only during certain phases of the selection process. A large number of both inducible and constitutive promoters are known.

In addition, it is possible to configure a retroviral vector to allow inducible expression of retroviral inserts after integration of a single vector in target cells; importantly, the entire system is contained within the single retrovirus. Tet-inducible retroviruses have been designed incorporating the Self-Inactivating (SIN) feature of 3' LTR enhancer/promoter retroviral deletion mutant (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, as defined below, which provide the candidate bioactive agents in a conformationally restricted or stable form; b) targeting sequences, defined below, which allow the localization of the candidate bioactive agent into a subcellular or extracellular compartment, particularly a nuclear localization sequence (NLS); c) rescue sequences as defined below, which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; f) reporter genes (preferably a labeling gene such as green fluorescent protein or a survival gene); or g) any combination of a), b), c), d), e), or f) as well as linker sequences as needed.

In a preferred embodiment, the fusion partner is a presentation structure. By "presentation structure" or grammatical equivalents herein is meant a sequence, which, when fused to candidate bioactive agents, causes the candidate agents to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

While the candidate bioactive agents may be either nucleic acid or peptides, presentation structures are preferably used with peptide candidate agents. Thus, synthetic presentation structures, i.e. artificial polypeptides, are capable of presenting a randomized peptide as a conformationally-restricted domain. Generally such presentation structures comprise a first portion joined to the N-terminal end of the randomized peptide, and a second portion joined to the C-terminal end of the peptide; that is, the peptide is inserted into the presentation structure, although variations may be made, as outlined below. To increase the functional isolation of the randomized expression product, the presentation structures are selected or designed to have minimal biologically activity when expressed in the target cell.

Preferred presentation structures maximize accessibility to the peptide by presenting it on an exterior loop. Accordingly, suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference). Using this system investigators have isolated peptides capable of high affinity interaction with the appropriate target. In general, coiled-coil structures allow for between 6 to 20 randomized positions.

A preferred coiled-coil presentation structure is as follows: MGC<u>AALESEVSALESEVASLE</u> <u>SEVAAL</u>GRGDMP<u>LAAVKSKL</u> <u>SAVKSKLASVKSKLAA</u>CGPP. The underlined regions represent a coiled-coil leucine zipper region defined previously (see Martin et al., EMBO J. 13(22):53035309 (1994), incorporated by reference). The bolded GRGDMP region represents the loop structure and when appropriately replaced with randomized peptides (i.e. candidate bioactive agents, generally depicted herein as $(X)_n$, where X is an amino acid residue and n is an integer of at least 5 or 6) can be of variable length. The replacement of the bolded region is facilitated by encoding restriction endonuclease sites in the underlined regions, which allows the direct incorporation of randomized oligonucleotides at these positions. For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, $Kd=10^{-7}$, for the pro-inflammatory cytokine IL-6.

A preferred minibody presentation structure is as follows: MGRNSQAT<u>SGFTFSHF</u>YMEWVRGGEYIAASR <u>HKHNKY</u>TTEYSASVKGRYIVSRDTSQSILYLQKKG PP. The bold, underline regions are the regions which may be randomized. The italized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred when secretory targeting sequences are used. As will be appreciated by those in the art, any number of random sequences, with or without spacer or linking sequences, may be flanked with cysteine residues. In other embodiments, effective presentation structures may be generated by the random regions themselves. For example, the random regions may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

In a preferred embodiment, the fusion partner is a targeting sequence that targets the candidate bioactive agent to a particular subcellular location. As will be appreciated by those in the art, the localization of proteins within a cell is a simple method for increasing effective concentration and determining function. The concentration of a protein can also be simply increased by nature of the localization. Shuttling the proteins into the nucleus confines them to a smaller space thereby increasing concentration. While other targeting sequences such as targeting sequences to the Golgi, endoplasmic reticulum, nuclear membrane, mitochondria, secretory vesicles, lysosome, and cellular membrane may be used, a preferred embodiment uses targeting sequences to the nucleus, i.e. a nuclear localization signal (NLS).

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLS's such as that of the SV40 (monkey virus) large T Antigen (Pro Lys Lys Lys Arg Lys Val), Kalderon (1984), et al., Cell, 39:499–509; the human retinoic acid receptor-β nuclear localization signal (ARRRRP); NF$_{\kappa B}$$_p$50 (EEVORKRQKL; Ghosh et al., Cell 62:1019 (1990); NF$_\kappa$B p65 (EEKRKRTYE; Nolan et al., Cell 64:961 (1991); and others (see for example Boulikas, J. Cell. Biochem. 55(1):32–58 (1994), hereby incorporated by reference) and double basic NLS's exemplified by that of the *Xenopus* (African clawed toad) protein, nucleoplasmin (Ala Val Lys Arg Pro Ala Ala Thr Lys Lys Ala Gly Gln Ala Lys Lys Lys Lys Leu Asp), Dingwall, et al., Cell, 30:449458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458462, 1990.

In a preferred embodiment, the fusion partner is a rescue sequence. A rescue sequence is a sequence which may be used to purify or isolate either the candidate agent or the nucleic acid encoding it. Thus, for example, peptide rescue sequences include purification sequences such as the His$_6$ tag for use with Ni affinity columns and epitope tags for detection, immunoprecipitation or FACS (fluoroscence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the candidate bioactive agent or the nucleic acid encoding it. Thus, for example, peptides may be stabilized by the incorporation of glycines after the initiation methionine (MG or MGG0), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows: MG(X)$_n$GGPP, where X is any amino acid and n is an integer of at least four.

In one embodiment, the fusion partner is a dimerization sequence. A dimerization sequence allows the non-covalent association of one random peptide to another random peptide, with sufficient affinity to remain associated under normal physiological conditions. This effectively allows small libraries of random peptides (for example, 104) to become large libraries if two peptides per cell are generated which then dimerize, to form an effective library of $10^8$ ($10^4 \times 10^4$). It also allows the formation of longer random peptides, if needed, or more structurally complex random peptide molecules. The dimers may be home or heterodimers.

Dimerization sequences may be a single sequence that self-aggregates, or two sequences, each of which is generated in a different retroviral construct. That is, nucleic acids encoding both a first random peptide with dimerization sequence 1, and a second random peptide with dimerization sequence 2, such that upon introduction into a cell and expression of the nucleic acid, dimerization sequence 1 associates with dimerization sequence 2 to form a new random peptide structure.

Suitable dimerization sequences will encompass a wide variety of sequences. Any number of protein—protein interaction sites are known. In addition, dimerization sequences may also be elucidated using standard methods such as the yeast two hybrid system, traditional biochemical affinity binding studies, or even using the present methods.

In a preferred embodiment, the fusion partner is a detection gene, preferably a labeling gene or a survival gene. That is, it is desirable to know that the candidate bioactive agent is a) present and b) being expressed. Thus, preferred embodiments utilize fusion constructs utilizing genes that allow the detection of cells that contain candidate bioactive agents. Preferred detection genes include, but are not limited to, green fluorescent proteins (GFP) from Aquorea victoria and Renilla species, as well as derivatives such as blue fluorescent protein (BFP), red fluorescent protein (RFP), yellow fluorescent protein (YFP), etc., as well as other labeling proteins such as luciferase (again, from any number of species including Renilla) and β-galactosidase.

In a preferred embodiment, as for the other constructs outlined herein, when a detection gene fusion partner is used with nucleic acid encoding a peptide candidate agent (which may also include other fusion partners as described herein), the two nucleic acids can be fused together in such a way as to only require a single promoter, i.e. using either an IRES site or a protease cleavage site such as 2a.

The fusion partners may be placed anywhere (i.e. N-terminal, C-terminal, internal) in the structure as the biology and activity permits.

In a preferred embodiment, the fusion partner includes a linker or tethering sequence, as generally described in PCT US 97/01019, that can allow the candidate agents to interact with potential targets unhindered. For example, when the candidate bioactive agent is a peptide, useful linkers include glycine-serine polymers (including, for example, $(GS)_n$, $(GSGGS)_n$ and $(GGGS)_n$, where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

In addition, the fusion partners, including presentation structures, may be modified, randomized, and/or matured to alter the presentation orientation of the randomized expression product. For example, determinants at the base of the loop may be modified to slightly modify the internal loop peptide tertiary structure, which maintaining the randomized amino add sequence.

In a preferred embodiment, combinations of fusion partners are used. Thus, for example, any number of combinations of presentation structures, targeting sequences, rescue sequences, and stability sequences may be used, with or without linker sequences.

Thus, candidate agents can include these components, and may then be used to generate a library of fragments, each containing a different random nucleotide sequence that may encode a different peptide. The ligation products are then transformed into bacteria, such as *E. coli*, and DNA is prepared from the resulting library, as is generally outlined in Kitamura, PNAS USA 92:9146–9150 (1995), hereby expressly incorporated by reference.

Delivery of the library DNA into a retroviral packaging system results in conversion to infectious virus. Suitable retroviral packaging system cell lines include, but are not limited to, the Bing and BOSC23 cell lines described in WO 94/19478; Soneoka et al., Nucleic Acid Res. 23(4):628 (1995); Finer et al., Blood 83:43 (1994); Pheonix packaging lines such as PhiNX-eco and PhiNX-ampho, described below; 292T+gag-pol and retrovirus envelope; PA317; and cell lines outlined in Markowitz et al., Virology 167:400 (1988), Markowitz et al., J. Virol. 62:1120 (1988), Li et al., PNAS USA 93:11658 (1996), Kinsella et al., Human Gene Therapy 7:1405 (1996), all of which are incorporated by reference.

Preferred systems include PhiNX-eco and PhiNX-ampho or similar cell lines, disclosed in PCT US97/01019.

In general, the candidate agents are added to the cells under reaction conditions that favor agent-target interactions. Generally, this will be physiological conditions. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. A variety of other reagents may be included in the assays. These include reagents like salts, neutral proteins, e.g. albumin, detergents, etc which may be used to facilitate optimal protein—protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Once the candidate agents have been introduced or combined with the cells containing the fusion constructs, a preferred embodiment includes stimulating the cells to produce germline mRNA. This may be done in a variety of ways, including the use of IL-4 and/or LPS. It should be noted that these stimulating compounds are not to be considered candidate agents for the purposes of the invention; thus "candidate agent" does not include molecules known to stimulate germline transcripts such as IL-4 and LPS.

Once the candidate agents have been added to the cells and the cells allowed to incubate for some period of time as needed, total mRNA is prepared from the cells to form an mRNA mixture. This can be done in a variety of ways, including the use of poly-T solid supports.

The isolation of mRNA comprises isolating total cellular RNA by disrupting a cell and performing differential centrifugation. Once the total RNA is isolated, mRNA is isolated by making use of the adenine nucleotide residues known to those skilled in the art as a poly (A) tail found on virtually every eukaryotic mRNA molecule at the 3'end thereof. Oligonucleotides composed of only deoxythymidine [olgo(dT)] are linked to cellulose and the oligo(dT)-cellulose packed into small columns When a preparation of total cellular RNA is passed through such a column, the mRNA molecules bind to the oligo(dT) by the poly (A) tails while the rest of the RNA flows through the column. The bound mRNAs are then eluted from the column and collected.

The isolation of total mRNA (and, if applicable, the creation of cDNA) forms a mixture herein referred to as the "mRNA mixture". Once the mRNA mixture is formed, at least one RNAse protection probe (RPP) is added to the mixture. RNAse protection probes are designed to be complementary to a germline transcript such that hybridization of the transcripts and the probes of the present invention occurs. Thus, the probes of the invention are essentially antisense molecules to the germline constructs. The transcripts to which the RPA probes hybridize are referred to herein as "target transcripts".

For hybridization to occur, complementarity between RPA probe and target transcript need not be perfect. There may be any number of base pair mismatches which will interfere with hybridization between the probes and transcripts, yet allow hybridization to occur. In this way, the RPA probe is substantially complementary to the target transcript. However, if the number of mismatches is so great that no hybridization can occur under even the least stringent of hybridization conditions, the mRNA (or cDNA) sequence is not a substantially complementary sequence, or target transcript of the RPA probe. Thus, by "substantially complementary" is meant that the probes are sufficiently complementary to the target sequences to hybridize under normal reaction conditions. Preferably, this complementarity is high enough to provide specificity, such that one probe will not hybridize to more than one transcript. In a preferred embodiment, the RPA probe sequences and target transcripts have less than 5 base mismatches, more preferably less than 3 base mismatches, and most preferably the RPA probe and the target transcript comprise complementary sequences having no base mismatches.

High stringency hybridization conditions are known in the art; see for example Maniatis, et al., *Molecular Cloning: A Laboratory Manual*, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at T, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

Further in regard to hybridization conditions, in one embodiment, experimental conditions including hybridization conditions are disclosed in the commercially available RPA III ™ Ribonuclease Protection Assay kit available from Ambion Inc., USA, catalog number 1414. Also disclosed in this kit are methods for normalizing RNAse protection.

RPA probes include for example the germline Igα-2 probe depicted in FIG. 3A (SEQ ID NO:1). This RPA probe comprises a nucleic acid sequence about 532 nucleotides in length. In a preferred embodiment, the present invention provides Igα-2 RPA probes consisting essentially of nucleotides from about 1 to about 530 of the Igα2 probe depicted in FIG. 3A. In another preferred embodiment, the present invention provides Igα2 RPA probes consisting essentially of nucleotides from about 1 or about 5 or about 10, to about 530 or about 520 or about 510 or about 500 or about 490 or about 480 or about 470 or about 460 or about 450 or about 440 or about 430 of the Igα2 probe depicted in FIG. 3A.

Also provided by the present invention is the germline Igα-2 probe depicted in FIG. 4A (SEQ ID NO:8). This RPA probe comprises a nucleic acid sequence about 430 nucleotides in length. The Igα-2 probe sequence depicted in FIG. 4A is preferred over the Igα-2 probe sequence depicted in FIG. 3A (SEQ ID NO: 1). In a preferred embodiment, the present invention provides Igα-2 RPA probes consisting essentially of nucleotides from about 1 to about 430 of the Igα2 probe depicted in FIG. 4A. In another preferred embodiment, the present invention provides Igα2 RPA probes consisting essentially of nucleotides from about 1 or about 5 or about 10, to about 430 or about 425 or about 420 or about 415 of the Igα2 probe depicted in FIG. 4A.

Also provided herein are Igα-2 RPA probes comprising nucleic acid sequences longer than that depicted in FIG. 3A (SEQ ID NO:1), which comprise the Igα-2 nucleic acid sequence depicted in FIG. 3 and additionally comprise about 5, or about 10, or about 15 additional nucleotides at the 3' terminus. Igα-2 probes are designed as complements of fragments of the nucleic acid sequence conceptually generated by fusion of the nucleic acid sequences depicted at Genbank accession numbers L04541 (being 5') and AL389978 (being 3'). The 3' nucleotides (up to about 15 nucleotides) of Igα-2 RPA probes which are in addition to the Igα2 probe sequence depicted in FIG. 3A comprise a nucleic acid sequence which is additionally complementary to the fused sequence of L04541 and AL389978 and contiguous with the preceding complementary sequence.

RPA probes include for example the germline Ig-epsilon probe depicted in FIG. 3A (SEQ ID NO:2). This RPA probe comprises a nucleic acid sequence about 202 nucleotides in length. In a preferred embodiment, the present invention provides Ig-epsilon RPA probes consisting essentially of nucleotides from about 1 to about 200 of the Ig-epsilon probe depicted in FIG. 3A. In another preferred embodiment, the present invention provides Ig-epsilon RPA probes consisting essentially of nucleotides from about 1 or about 5 or about 10, to about 200 or about 195 or about 190 or about 185 of the Ig-epsilon probe depicted in FIG. 3A.

Also provided by the present invention is the germline Ig-epsilon probe depicted in FIG. 4A (SEQ ID NO:9). This RPA probe comprises a nucleic acid sequence about 202 nucleotides in length. In a preferred embodiment, the present invention provides Ig-epsilon RPA probes consisting essentially of nucleotides from about 1 to about 200 of the Ig-epsilon probe depicted in FIG. 4A. In another preferred embodiment, the present invention provides Ig-epsilon RPA probes consisting essentially of nucleotides from about 1 or about 5 or about 10, to about 200 or about 195 or about 190 or about 185 of the Ig-epsilon probe depicted in FIG. 4A.

Also provided herein are Ig-epsilon RPA probes comprising nucleic acid sequences longer than that depicted in FIG. 3A (SEQ ID NO:2), which comprise the Ig-epsilon nucleic acid sequence depicted in FIG. 3 and additionally comprise about 5, or about 10, or about 15 additional nucleotides at the 3' terminus. Ig-epsilon probes are designed as complements of fragments of the nucleic acid sequence conceptually generated by fusion of the nucleic acid sequences depicted at Genbank accession numbers X56797 (being 5') and J00222 (being 3'). The 3' nucleotides (up to about 15 nucleotides) of Ig-epsilon RPA probes which are in addition to the Ig-epsilon probe sequence depicted in FIG. 3A comprise a nucleic acid sequence which is additionally complementary to the fused sequence of X56797 and J00222 and contiguous with the preceding complementary sequence.

RPA probes include for example the germline Ig gamma-1 probe depicted in FIG. 3A (SEQ ID NO:3). This RPA probe comprises a nucleic acid sequence about 593 nucleotides in length. In a preferred embodiment, the present invention provides Ig gamma-1 RPA probes consisting essentially of nucleotides from about 1 to about 590 of the Ig gamma-1 probe depicted in FIG. 3A. In another preferred embodiment, the present invention provides Ig gamma-1 RPA probes consisting essentially of nucleotides from about 1 or about 5 or about 10, to about 590 or about 580 or about 570 or about 560 or about 550 or about 540 or about 530 or about 520 or about 510 or about 500 or about 490 or about 480 or about 470 or about 460 or about 450 or about 440 or about 430 or about 420 or about 410 or about 400 or about 390 or about 380 or about 370 of the Ig gamma-1 probe depicted in FIG. 3A.

Also provided by the present invention is the germline Ig gamma-1 probe depicted in FIG. 4A (SEQ ID NO:10). This RPA probe comprises a nucleic acid sequence about 370 nucleotides in length. The Ig gamma-1 probe sequence depicted in FIG. 4A is preferred over the Ig gamma-1 probe sequence depicted in FIG. 3A (SEQ ID NO:3). In a preferred embodiment, the present invention provides Ig gamma-1 RPA probes consisting essentially of nucleotides from about 1 to about 370 of the Ig gamma-1 probe depicted in FIG. 4A. In another preferred embodiment, the present invention provides Ig gamma-1 RPA probes consisting essentially of nucleotides from about 1 or about 5 or about 10, to about 370 or about 365 or about 360 or about 355 of the Ig gamma-1 probe depicted in FIG. 4A.

Also provided herein are Ig gamma-1 RPA probes comprising nucleic acid sequences longer than that depicted in FIG. 3A (SEQ ID NO:3), which comprise the Ig gamma-1 nucleic acid sequence depicted in FIG. 3A and additionally comprise about 5, or about 10, or about 15 additional nucleotides at the 3' terminus. Ig gamma-1 probes are designed as complements of fragments of the nucleic acid sequence conceptually generated by fusion of the nucleic acid sequences depicted at Genbank accession numbers AL122127 (being 5') and Z17370 (being 3'). The 3 nucleotides (up to about 15 nucleotides) of Ig gamma-1 RPA probes which are in addition to the Ig gamma-1 probe sequence depicted in FIG. 3A comprise a nucleic acid sequence which is additionally complementary to the fused sequence of AL122127 and Z17370 and contiguous with the preceding complementary sequence.

RPA probes include for example the germline Ig gamma-2 probe depicted in FIG. 3B (SEQ ID NO:4). This RPA probe comprises a nucleic acid sequence about 632 nucleotides in length. In a preferred embodiment, the present invention provides Ig gamma-2 RPA probes consisting essentially of nucleotides from about 1 to about 630 of the Ig gamma-2 probe depicted in FIG. 3B. In another preferred embodiment, the present invention provides Ig gamma-2 RPA probes consisting essentially of nucleotides from about 1 or about 5 or about 10, to about 630 or about 620 or about 610 or about 600 or about 590 or about 580 or about 570 or about 560 or about 550 or about 540 or about 530 or about 520 or about 510 or about 500 or about 490 or about 480 or about 470 or about 460 or about 450 or about 440 or about 430 or about 420 or about 410 or about 400 or about 390 or about 380 of the Ig gamma-2 probe depicted in FIG. 3B.

Also provided by the present invention is the germline Ig gamma-2 probe depicted in FIG. 4B (SEQ ID NO:11). This RPA probe comprises a nucleic acid sequence about 387 nucleotides in length. The Ig gamma-2 probe sequence depicted in FIG. 4B is preferred over the Ig gamma-2 probe sequence depicted in FIG. 3B (SEQ ID NO:4). In a preferred embodiment, the present invention provides Ig gamma-2 RPA probes consisting essentially of nucleotides from about 1 to about 385 of the Ig gamma-2 probe depicted in FIG. 4B. In another preferred embodiment, the present invention provides Ig gamma-2 RPA probes consisting essentially of nucleotides from about 1 or about 5 or about 10 to about 385 or about 380 or about 375 or about 370 of the Ig gamma-2 probe depicted in FIG. 4B.

Also provided herein are Ig gamma-2 RPA probes comprising nucleic acid sequences longer than that depicted in FIG. 3B (SEQ ID NO:4), which comprise the Ig gamma-2 nucleic acid sequence depicted in FIG. 3B and additionally comprise about 5, or about 10, or about 15 additional nucleotides at the 3' terminus. Ig gamma-2 probes are designed as complements of fragments of the nucleic acid sequence conceptually generated by fusion of the nucleic acid sequences depicted at Genbank accession numbers U39934 (being 5') and J00230 (being 3'). The 3' nucleotides (up to about 15 nucleotides) of Ig gamma-2 RPA probes which are in addition to the Ig gamma-2 probe sequence depicted in FIG. 3B comprise a nucleic acid sequence which is additionally complementary to the fused sequence of U39934 and J00230 and contiguous with the preceding complementary sequence.

RPA probes include for example the germline Ig gamma-3 probe depicted in FIG. 3B (SEQ ID NO:5). This RPA probe comprises a nucleic acid sequence about 650 nucleotides in length. In a preferred embodiment, the present invention provides Ig gamma-3 RPA probes consisting essentially of nucleotides from about 1 to about 650 of the Ig gamma-3 probe depicted in FIG. 3B. In another preferred embodiment, the present invention provides Ig gamma-3 RPA probes consisting essentially of nucleotides from about 1 or about 5 or about 10, to about 650 or about 640 or about 630 or about 620 or about 610 or about 600 or about 590 or about 580 or about 570 or about 560 or about 550 or about 540 or about 530 or about 520 or about 510 or about 500 or about 490 or about 480 or about 470 or about 460 or about 450 or about 440 or about 430 or about 420 or about 410 or about 400 or about 390 of the Ig gamma-3 probe depicted in FIG. 3B.

Also provided by the present invention is the germline Ig gamma-3 probe depicted in FIG. 4B (SEQ ID NO:12). This RPA probe comprises a nucleic acid sequence about 391 nucleotides in length. The Ig gamma-3 probe sequence depicted in FIG. 4B is preferred over the Ig gamma-3 probe sequence depicted in FIG. 3B (SEQ ID NO:5). In a preferred embodiment, the present invention provides Ig gamma-3 RPA probes consisting essentially of nucleotides from about 1 to about 390 of the Ig gamma-3 probe depicted in FIG. 4B. In another preferred embodiment, the present invention provides Ig gamma-3 RPA probes consisting essentially of nucleotides from about 1 or about 5 or about 10, to about 390 or about 385 or about 380 or about 375 of the Ig gamma-3 probe depicted in FIG. 4B.

Also provided herein are Ig gamma-3 RPA probes comprising nucleic acid sequences longer than that depicted in FIG. 3B (SEQ ID NO:5), which comprise the Ig gamma-3 nucleic acid sequence depicted in FIG. 3B and additionally comprise about 5, or about 10, or about 15 additional nucleotides at the 3' terminus. Ig gamma-3 probes are designed as complements of fragments of the nucleic acid sequence conceptually generated by fusion of the nucleic acid sequences depicted at Genbank accession numbers AL122127 (being 5') and X16110 (being 3'). The 3' nucleotides (up to about 15 nucleotides) of Ig gamma-3 RPA probes which are in addition to the Ig gamma-3 probe sequence depicted in FIG. 3B comprise a nucleic acid sequence which is additionally complementary to the fused sequence of AL122127 and X16110 and contiguous with the preceding complementary sequence.

RPA probes include for example the germline Ig gamma-4 probe depicted in FIG. 3B (SEQ ID NO:6). This RPA probe comprises a nucleic acid sequence about 706 nucleotides in length. In a preferred embodiment, the present invention provides Ig gamma-4 RPA probes consisting essentially of nucleotides from about 1 to about 705 of the Ig gamma-4 probe depicted in FIG. 3B. In another preferred embodiment, the present invention provides Ig gamma-4 RPA probes consisting essentially of nucleotides from about 1 or about 5 or about 10, to about 705 or about 695 or about 685 or about 675 or about 665 or about 655 or about 645 or about 635 or about 625 or about 615 or about 605 or about 595 or about 585 or about 575 or about 565 or about 555 or about 545 or about 535 or about 525 or about 515 or about 505 or about 495 of the Ig gamma-4 probe depicted in FIG. 3B.

Also provided by the present invention is the germ line Ig gamma-4 probe depicted in FIG. 4B (SEQ ID NO:13). This RPA probe comprises a nucleic acid sequence about 497 nucleotides in length. The Ig gamma-4 probe sequence depicted in FIG. 4B is preferred over the Ig gamma-4 probe sequence depicted in FIG. 3B (SEQ ID NO:6). In a preferred embodiment, the present invention provides Ig gamma-4 RPA probes consisting essentially of nucleotides from about 1 to about 495 of the Ig gamma-4 probe depicted in FIG. 4B. In another preferred embodiment, the present invention provides Ig gamma-4 RPA probes consisting essentially of nucleotides from about 1 or about 5 or about 10, to about 495 or about 490 or about 485 or about 480 of the Ig gamma-4 probe depicted in FIG. 4B.

Also provided herein are Ig gamma-4 RPA probes comprising nucleic acid sequences longer than that depicted in FIG. 3B (SEQ ID NO:6), which comprise the Ig gamma-4 nucleic acid sequence depicted in FIG. 3B and additionally comprise about 5, or about 10, or about 15 additional nucleotides at the 3' terminus. Ig gamma-4 probes are designed as complements of fragments of the nucleic acid sequence conceptually generated by fusion of the nucleic acid sequences depicted at Genbank accession numbers X56796 (being 5') and K01316 (being 3'). The 3' nucleotides (up to about 15 nucleotides) of Ig gamma-4 RPA probes which are in addition to the Ig gamma-4 probe sequence depicted in FIG. 3B comprise a nucleic acid sequence which is additionally complementary to the fused sequence of X56796 and K01316 and contiguous with the preceding complementary sequence.

RPA probes include for example the germline Igα-1 probe depicted in FIG. 4A (SEQ ID NO:7). This RPA probe comprises a nucleic acid sequence about 400 nucleotides in length. In a preferred embodiment, the present invention provides Igα-1 RPA probes consisting essentially of nucleotides from about 1 to about 400 of the Igα-1 probe depicted in FIG. 4A. In another preferred embodiment, the present invention provides Igα-1 RPA probes consisting essentially of nucleotides from about 1 or about 6 or about 10, to about 400 or about 395 or about 390 or about 385 of the Igα-1 probe depicted in FIG. 4A.

Also provided herein are Igα-1 RPA probes comprising nucleic acid sequences longer than that depicted in FIG. 4A (SEQ ID NO:7), which comprise the Igα-1 nucleic acid sequence depicted in FIG. 4A and additionally comprise about 5, or about 10, or about 15 additional nucleotides at the 3' terminus. Igα-1 probes are designed as complements of fragments of the nucleic acid sequence conceptually generated by fusion of the nucleic acid sequences depicted at Genbank accession numbers L04541 (being 5') and BC005951 (being 3'). The 3' nucleotides (up to about 15 nucleotides) of Igα-1 RPA probes which are in addition to the Igα-1 probe sequence depicted in FIG. 4A comprise a nucleic acid sequence which is additionally complementary to the fused sequence of L04541 and BC005951 and contiguous with the preceding complementary sequence.

In a preferred embodiment, RPA probes consist essentially of nucleic acid sequences selected from the group consisting of the set of Igα-1, Igα-2, 1 g-epsilon, Ig gamma-1, Ig gamma-2, Ig gamma-3 and Ig gama-4 RPA probes described herein. Preferably, the RPA probes exclude vector nucleic acids. Preferably, the RPA probes exclude genomic DNA.

RPA probes are sometimes referred to herein as "probes".

Preferred probe sequences are directed to the germline transcripts of IgA1, IgA2, IgE, IgG1, IgG2, IgG3 and IgG4.

Preferred probe sequences of the invention are shown in the figures. FIGS. 3A–3B (SEQ ID NOS:1–6) depict some "longer" probes and FIGS. 4A–4B (SEQ ID NOS:7–13) some shorter, preferred versions. Thus, preferred probes include nucleic acids consisting essentially of the sequences shown in FIGS. 3A–3B or 4A–4B.

In some embodiments, the complements of the probes shown in the Figures are used.

In a preferred embodiment, the RPPs comprise labels. By "label" herein is meant an element (e.g. an isotope) or chemical compound that is attached to enable the detection of the compound. Preferred labels include radioactive isotopic labels, enzymes, and colored or fluorescent dyes. In some instances labels such as magnetic beads, or indirect labels that can be attached to any of the primary labels can be used. The labels may be incorporated into the compound at any position and may be attached through linkers.

A preferred embodiment utilizes radioisotopes such as $P^{32}$.

In a preferred embodiment, the RPPs can also comprise or encode a purification tag, as is outlined above for fusion partners.

In a preferred embodiment, RPPs corresponding to housekeeping genes are added to serve as internal controls. Suitable housekeeping genes will vary with the cell type used, and include, but are not limited to, cyclophilin.

The RPPs and the mRNA mixture comprising the germline transcripts of the invention (or corresponding cDNA mixture and cDNA of transcripts) are combined under conditions that favor the formation of hybridization complexes.

Once the hybridization complexes are formed, at least one RNAse protection enzyme (RPE) is added to the mixture comprising the hybridization complexes. RNAse protection enzymes are enzymes that digest single stranded nucleic acids (particularly RNA) but do not digest double stranded nucleic acids (e.g. the complex of the probe and germline transcript). A variety of RPEs are known, including, but not limited to, RNAse A and RNAse T1, with mixtures of the two being preferred. Commercial kits for these assays are also known.

The addition of the enzyme allows the removal or digestion of any mRNA that does not correspond to the probe sequences. That is, any single stranded nucleic acids in the mRNA mixture are digested by the RPE, leaving only double stranded nucleic acids.

Once the non-hybridized mRNA (i.e. single stranded) is digested away or removed, the amount of germline transcript (hybridized to RPA probe) is detected and/or quantified. This can be done in a variety of ways, and can be done with denaturation into single stranded forms if required. Frequently gel electrophoresis is used, although other types of size exclusion techniques may be used, or other separation steps. The amount of germline transcript present is inferred by determining the amount of RPA probe protected from RNAse digestion. Quantification can be done by normalizing to the level of RNAse protected transcripts of housekeeping genes between samples.

The present invention allows a variety of new assays and compositions. One advantage of the present invention is that by using sets of probes directed to different germline transcripts, bioactive agents that modulate the production of more than one germline transcript can be evaluated. Similarly, agents that modulate only one of the germline transcripts and do not modulate others may be found. For example, using the set of RPPs in these assays, and testing a variety of compounds, modulators, particularly inhibitors, of IgE but not IgA or IgG can be found.

The level of multiple transcripts may be determined simultaneously using multiple distinct RPA probes directed to distinct germ line transcripts (i.e. designed to be complements of distinct germ line transcripts) and having different lengths. The individual protected RPA probes may be resolved, following hybridization with isolated mRNA and exposure to RNAse, by gel electrophoresis against standards or probe samples. Such resolution allows the probes to be identified based on size, and in this way, the levels of multiple germ line transcripts may be determined in a single experiment.

In a preferred embodiment, the present invention provides kits including one or more of the RPPs depicted in the Figures or described herein. The kits optionally contain instructions, enzymes, and any other reagents required, including labeling reagents.

As discussed herein, by providing more than one germline probe selected from the group consisting of the set of Igα-1, Igα-2, Ig-epsilon, Ig gamma-1, Ig gamma-2, Ig gamma-3 and Ig gama4 RPA probes described herein, and preferably by providing at least one RPA probe from each Ig group (i.e. at least one probe from the set of RPA probes for Igα1, and at least one probe from the set of RPA probes for Igα2, etc.), the present invention provides a composition which allows determination of a profile of germline transcripts rather than a single germline transcript, which is highly preferred.

All references and nucleic acid sequences at accession numbers cited are herein incorporated by reference.

EXAMPLE

Probes were designed to span two or more exons to specifically detect spliced messages. Mismatched base pairs between the probe and the RNA sample are digested resulting in multiple fragments distinguishable by size from the protected fragment of interest. Protected fragments of the correct size distinguish correctly spliced mRNA from genomic DNA, unspliced or aberrantly spliced mRNA, and spliced messages containing exons different from those of the probe such as mature spliced antibody mRNA.

Generating a set of Human Probes

Oligo primers were designed to amplify each of the germline transcripts for IgA1, IgA2, IgE, IgG1, IgG2, IgG3 and IgG4. The 5' primer in each case is situated within the intervening exon (1-exon) which is an exon uniquely transcribed in germline Ig transcripts as switch recombination results in the deletion of this exon from the genome (FIGS. 1 and 2). The 3' primers are either in the first heavy chain constant exon (CH-1) as in the IgE probe, or in the heavy chain constant hinge exon (C-hinge) as in all of the IgG probes (FIG. 8). Primers were designed within regions having the least homology using sequence alignments of closely relate genes with the exception of the 5' primer used to amplify both IgG1 and IgG3. Probes were amplifed by standard PCR methods from either a cDNA library made from primary human B and T cells cultured in a cocktail of cytokines which cause switch recombination to IgE in B cells after 2 weeks (from pooled RNAs from several days) or from cDNA made from total human spleen RNA. All 5' primers contain a HindIII restriction site and all 3' primers contain a BamHI site allowing the PCR fragments to be cloned in a convenient vector containing a T7 RNA polymerase promoter using standard methods in the orientation for transcription of antisense message (FIG. 9). Multiple clones from each bacterial transformation were sequenced by standard methods to identify correct probes. All probes except IgE were shortened after cloning by removing portions of the 3' ends. The shortened probes are preferred herein.

RPA using Probes for Human Ig Germline Transcripts to Screen Modulators

The standard method for carrying out an RPA assay is to radiolabel an antisense RNA copy of a probe by in vitro transcription using a bacterial promoter and NTPs one of which is an $\alpha^{32}P$ NTP. Probes can also be labeled with other radioactive dNTPs or nonradioactive reagents such as fluorochromes or other detectable moieties during or after the transcription reaction. Kits for performing this assay are commercially available. The antisense probe is then hybridized in excess with a limiting amount of cellular total or polyA+ RNA. The same amount of cellular RNA is also hybridized to radiolabeled probes for internal housekeeping gene transcripts such as cyclophilin. These probes are commercially available. The RNA hybrids are then digested with either RNAse T1 or RNAse T1 and RNAse A to remove all single stranded regions of RNA. The antisense probes are optionally additionally incubated with nonhybridizing RNA such as yeast RNA and then digested as a positive control for the completeness of digestion. The remaining double stranded RNA is then electrophoresed in an acrylamide-UREA containing gel along with labeled size markers and undigested antisense probe. The bands are visualized using beta imaging equipment or exposure of imaging film, or other detection techniques depending on the label. A typical result could be that the lane loaded with undigested probe or probes would contain bands of the size of the full-length probe. Lanes containing nonhybridizing and digested RNA would contain no bands or faint bands of full-length residual undigested probe. Lanes containing cellular RNA hybridized to probe or probes and digested would contain the predicted protected fragment if the cells from which the RNA was extracted produce the transcript of interest. If bands appear that are smaller than the predicted protected fragment the cells produce a transcript containing one or more exon, partial or complete, contained in the probe but not the transcript of interest. If no band appears the cells are not making a detectable amount of any transcript containing any of the exons that are in the probe. Utilizing the probe set for human germline immunoglobulin transcripts any measurable change in the level of germline transcript produced can be quantified. The intensity of the protected probe fragment band signal is directly correlated with the amount of germline transcript present in the cells. Quantification can be carried out between one or more probes in the same sample of RNA or between samples of RNA by normalizing for the expression of internal housekeeping standard transcripts (data not shown). Whole animals, cell cultures from primary tissue, or established cell lines can be treated with peptides, small molecules, cDNAs, cytokines or other modifiers and the extracted RNA can be examined using the RPA probes for expression of germline transcripts (data not shown).

We claim:

1. A method for determining whether a candidate agent is capable of modulating germline transcription, comprising:
   a) adding a candidate agent to a plurality of cells
   b) preparing mRNA from said plurality of cells to form an mRNA mixture;
   c) adding to said mixture at least a first RNAse protection probe (RPP) substantially complementary to a first germline mRNA from an immunoglobulin heavy chain gene locus to form a first hybridization complex between said first germline mRNA and said first RPP, wherein said RPP has a sequence selected from the group consisting of the sequences depicted in FIG. 3 (SEQ ID NOS: 1–6);
   d) adding an RNAse protection enzyme (RPE) to said mixture, such that mRNA that is not protected is digested; and
   e) quantifying the amount of said first germline mRNA as compared to a cell in the absence of a candidate agent, to thereby identify a candidate agent that alters the amount of said first germline mRNA.

2. A method for determining whether a candidate agent is capable of modulating germline transcription, comprising:
   a) adding a candidate agent to a plurality of cells
   b) preparing mRNA from said plurality of cells to form an mRNA mixture;
   c) adding to said mixture at least a first RNAse protection probe (RPP) substantially complementary to a first germline mRNA from an immunoglobulin heavy chain gene locus to form a first hybridization complex between said first germline mRNA and said first RPP, wherein said RPP has a sequence selected from the group consisting of the sequences depicted in FIG. 4 (SEQ ID NOS:7–13);
   d) adding an RNAse protection enzyme (RPE) to said mixture, such that mRNA that is not protected is digested; and
   e) quantifying the amount of said first germline mRNA as compared to a cell in the absence of a candidate agent to thereby identify a candidate agent that alters the amount of said first germline mRNA.

3. A method for determining whether a candidate agent is capable of modulating germline transcription, comprising:
   a) adding a candidate agent to a plurality of cells
   b) preparing mRNA from said plurality of cells to form an mRNA mixture;
   c) adding to said mixture at least a first RNAse protection probe (RPP) substantially complementary to a first germline mRNA from an immunoglobulin heavy chain gene locus to form a first hybridization complex between said first germline mRNA and said first RPP, wherein said germline mRNA is Ig alpha-1, and wherein said RPP comprises the sequence set forth as SEQ ID NO:7;
   d) adding an RNAse protection enzyme (RPE) to said mixture, such that mRNA that is not protected is digested; and
   e) quantifying the amount of said first germline mRNA as compared to a cell in the absence of a candidate agent to thereby identify a candidate agent that alters the amount of said first germline mRNA.

4. A method for determining whether a candidate agent is capable of modulating germline transcription, comprising:
   a) adding a candidate agent to a plurality of cells
   b) preparing mRNA from said plurality of cells to form an mRNA mixture;
   c) adding to said mixture at least a first RNAse protection probe (RPP) substantially complementary to a first germline mRNA from an immunoglobulin heavy chain gene locus to form a first hybridization complex between said first germline mRNA and said first RPP, wherein said germline mRNA is Ig alpha-2, and wherein said RPP comprises the sequence set forth as SEQ ID NO:1 or SEQ ID NO:8;

d) adding an RNAse protection enzyme (RPE) to said mixture, such that mRNA that is not protected is digested; and e) quantifying the amount of said first germline mRNA as compared to a cell in the absence of a candidate agent to thereby identify a candidate agent that alters the amount of said first germline mRNA.

5. A method for determining whether a candidate agent is capable of modulating germline transcription, comprising:

a) adding a candidate anent to a plurality of cells b) preparing mRNA from said plurality of cells to form an mRNA mixture;

c) adding to said mixture at least a first RNAse protection probe (RPP) substantially complementary to a first germline mRNA from an immunoglobulin heavy chain gene locus to form a first hybridization complex between said first germline mRNA and said first RPP, wherein said germline mRNA is Ig epsilon, and wherein said RPP comprises the sequence set forth as SEQ ID NO:2 or SEQ ID NO:9;

d) adding an RNAse protection enzyme (RPE) to said mixture, such that mRNA that is not protected is digested; and e) quantifying the amount of said first germline mRNA as compared to a cell in the absence of a candidate agent to thereby identify a candidate agent that alters the amount of said first germline mRNA.

6. A method for determining whether a candidate agent is capable of modulating germline transcription, comprising:

a) adding a candidate agent to a plurality of cells b) preparing mRNA from said plurality of cells to form an mRNA mixture;

c) adding to said mixture at least a first RNAse protection probe (RPP) substantially complementary to a first germline mRNA from an immunoglobulin heavy chain gene locus to form a first hybridization complex between said first germline mRNA and said first RPP, wherein said germline mRNA is Ig gamma-1, and wherein said RPP comprises the sequence set forth as SEQ ID NO:3 or SEQ ID NO:10, d) adding an RNAse protection enzyme (RPE) to said mixture, such that mRNA that is not protected is digested; and e) quantifying the amount of said first germline mRNA as compared to a cell in the absence of a candidate agent to thereby identify a candidate agent that alters the amount of said first germline mRNA.

7. A method for determining whether a candidate agent is capable of modulating germline transcription, comprising:

a) adding a candidate agent to a plurality of cells b) preparing mRNA from said plurality of cells to form an mRNA mixture;

c) adding to said mixture at least a first RNAse protection probe (RPP) substantially complementary to a first germline mRNA from an immunoglobulin heavy chain gene locus to form a first hybridization complex between said first germline mRNA and said first RPP, wherein said germline mRNA is Ig gamma-2, and wherein said RPP comprises the sequence set forth as SEQ ID NO:4 or SEQ ID NO:11;

d) adding an RNAse protection enzyme (RPE) to said mixture, such that mRNA that is not protected is digested; and e) quantifying the amount of said first germline mRNA as compared to a cell in the absence of a candidate agent to thereby identify a candidate agent that alters the amount of said first germline mRNA.

8. A method for determining whether a candidate agent is capable of modulating germline transcription, comprising:

a) adding a candidate agent to a plurality of cells b) preparing mRNA from said plurality of cells to form an mRNA mixture;

c) adding to said mixture at least a first RNAse protection probe (RPP) substantially complementary to a first germline mRNA from an immunoglobulin heavy chain gene locus to form a first hybridization complex between said first germline mRNA and said first RPP, wherein said germline mRNA is Ig gamma-3, and wherein said RPP comprises the sequence set forth as SEQ ID NO:5 or SEQ ID NO:12;

d) adding an RNAse protection enzyme (RPE) to said mixture, such that mRNA that is not protected is digested; and e) quantifying the amount of said first germline mRNA as compared to a cell in the absence of a candidate agent to thereby identify a candidate agent that alters the amount of said first germline mRNA.

9. A method for determining whether a candidate agent is capable of modulating germline transcription, comprising:

a) adding a candidate agent to a plurality of cells b) preparing mRNA from said plurality of cells to form an mRNA mixture;

c) adding to said mixture at least a first RNAse protection probe (RPP) substantially complementary to a first germ line mRNA from an immunoglobulin heavy chain gene locus to form a first hybridization complex between said first germline mRNA and said first RPP, wherein said germline mRNA is Ig gamma-4, and wherein said RPP comprises the sequence set forth as SEQ-ID NO:6 or SEQ ID NO:1.3;

(d) adding an RNAse protection enzyme (RPE) to said mixture, such that mRNA that is not protected is digested; and (e) quantifying the amount of said first germline mRNA as compared to a cell in the absence of a candidate agent to thereby identify a candidate agent that alters the amount of said germline mRNA.

10. A method according to any one of claim 1, 2, 3, 4, 5, 6, 7, 8, or 9, further comprising stimulating said cells to produce germline mRNA.

11. A method according to any one of claim 1, 2, 3, 4, 5, 6, 7, 8, or 9, wherein said RPP is labeled.

12. A method according to claim 11, wherein said label is a fluorescent label..

13. A method according to claim 11, wherein said label is a radioisotope.

14. A method according to any one of claim 1, 2, 3, 4, 5, 6, 7, 8, or 9, further comprising:

a) adding to said mixture at least a second RNAse protection probe (RPP) substantially complementary to a second germline mRNA to form a second hybridization complex between said second germline mRNA and said second RPP; and b) quantifying the amount of said second germline mRNA as compared to a cell in the absence of a candidate agent to thereby identify a candidate agent that alters the amount of said first germline mRNA but not said second germline mRNA.

15. A method according to any one of claim 1, 2, 3, 4, 5, 6, 7, 8, or 9, wherein said candidate agent is a small molecule.

16. A method according to any one of claim 1, 2, 3, 4, 5, 6, 7, 8, or 9, wherein said candidate agent is a peptide.

17. A method according to claim 16, wherein said peptide is a random peptide.

18. A method according to claim 16, wherein said peptide is a partially random peptides.

19. A method according to claim 16, wherein said adding is done using a retrovirus encoding said peptide.

20. A method according to claim 16 wherein said adding is done using a retrovirus comprising sequence derived from a cDNA library.

21. The method of any one of claim 1, 2, 3, 4, 5, 6, 7, 8, or 9, wherein said first RNAse protection probe (RPP) and said first germline mRNA contain less than 5 base mismatches.

* * * * *